(12) United States Patent
Alcaide et al.

(10) Patent No.: US 12,001,602 B2
(45) Date of Patent: Jun. 4, 2024

(54) BRAIN-COMPUTER INTERFACE WITH ADAPTATIONS FOR HIGH-SPEED, ACCURATE, AND INTUITIVE USER INTERACTIONS

(71) Applicant: Neurable Inc., Boston, MA (US)

(72) Inventors: Ramses Alcaide, Boston, MA (US); Dereck Padden, Newton, MA (US); Jay Jantz, Burlington, MA (US); James Hamet, Cambridge, MA (US); Jeffrey Morris, Jr., Cambridge, MA (US); Arnaldo Pereira, Acton, MA (US)

(73) Assignee: Neurable Inc., Boston, MA (US)

( * ) Notice: Subject to any disclaimer, the term of this patent is extended or adjusted under 35 U.S.C. 154(b) by 240 days.

(21) Appl. No.: 16/872,730

(22) Filed: May 12, 2020

(65) Prior Publication Data
US 2020/0268296 A1    Aug. 27, 2020

Related U.S. Application Data

(63) Continuation of application No. PCT/US2018/060797, filed on Nov. 13, 2018.
(Continued)

(51) Int. Cl.
*A61B 5/16*        (2006.01)
*G06F 3/01*        (2006.01)
*G06F 3/04842*     (2022.01)

(52) U.S. Cl.
CPC .............. *G06F 3/013* (2013.01); *G06F 3/015* (2013.01); *G06F 3/017* (2013.01); *G06F 3/04842* (2013.01); *G06F 2203/0381* (2013.01)

(58) Field of Classification Search
CPC ....... A61B 5/7267; A61B 5/378; A61B 5/163; G06F 3/015; G06F 3/017; G06F 3/04842;
(Continued)

(56) References Cited

U.S. PATENT DOCUMENTS

| 4,013,068 A | 3/1977 | Settle et al. |
| 4,158,196 A | 6/1979 | Crawford, Jr. |

(Continued)

FOREIGN PATENT DOCUMENTS

| CA | 2765500 A1 | 12/2010 |
| CN | 1927551 A  | 3/2007 |

(Continued)

OTHER PUBLICATIONS

Amyotrophic Lateral Sclerosis (ALS) Fact Sheet, National Institute of Neurological Disorders and Stroke (Jun. 2013), 12 pages.
(Continued)

*Primary Examiner* — Christopher E Leiby
(74) *Attorney, Agent, or Firm* — COOLEY LLP

(57) ABSTRACT

Embodiments described herein relate to systems, devices, and methods for use in the implementation of a brain-computer interface that integrates real-time eye-movement tracking with brain activity tracking to present and update a user interface that is strategically designed for high speed and accuracy of human-machine interaction. Embodiments described herein also relate to the implementation of a hardware agnostic brain-computer interface with specific user interface adaptations to enable high-speed, intuitive, and accurate user manipulation of applications and/or machines.

23 Claims, 14 Drawing Sheets

Related U.S. Application Data

(60) Provisional application No. 62/585,209, filed on Nov. 13, 2017.

(58) Field of Classification Search
CPC .. G06F 3/013; G06F 2203/0381; G16H 50/70
See application file for complete search history.

(56) References Cited

U.S. PATENT DOCUMENTS

| | | | |
|---|---|---|---|
| 4,595,990 A | 6/1986 | Garwin et al. |
| 5,137,027 A | 8/1992 | Rosenfeld |
| 5,213,338 A | 5/1993 | Brotz |
| 5,269,325 A | 12/1993 | Robinson et al. |
| 5,325,862 A | 7/1994 | Lewis et al. |
| 5,339,826 A | 8/1994 | Schmidt et al. |
| 5,342,410 A | 8/1994 | Braverman |
| 5,467,777 A | 11/1995 | Farwell |
| 5,638,826 A | 6/1997 | Wolpaw et al. |
| 5,692,517 A | 12/1997 | Junker |
| 5,742,286 A | 4/1998 | Kung et al. |
| 5,899,867 A | 5/1999 | Collura |
| 5,931,908 A | 8/1999 | Gerba et al. |
| 5,967,996 A | 10/1999 | Kadota et al. |
| 5,983,129 A | 11/1999 | Cowan et al. |
| 6,090,051 A | 7/2000 | Marshall |
| 6,323,884 B1 | 11/2001 | Bird et al. |
| 6,380,937 B1 | 4/2002 | Dong et al. |
| 6,712,468 B1 | 3/2004 | Edwards |
| 6,847,844 B2 | 1/2005 | Sun et al. |
| 6,917,370 B2 | 7/2005 | Benton |
| 7,084,884 B1 | 8/2006 | Nelson et al. |
| 7,120,486 B2 | 10/2006 | Leuthardt et al. |
| 7,546,158 B2 | 6/2009 | Allison et al. |
| 7,580,742 B2 | 8/2009 | Tan et al. |
| 7,835,787 B2 | 11/2010 | Sajda et al. |
| 8,155,736 B2 | 4/2012 | Sullivan et al. |
| 8,244,475 B2 | 8/2012 | Aguilar et al. |
| 8,594,814 B2 | 11/2013 | Rovaglio et al. |
| 8,878,785 B1 | 11/2014 | Nordstrom |
| 9,183,560 B2 | 11/2015 | Abelow |
| 9,210,517 B2 | 12/2015 | Pontoppidan et al. |
| 9,389,685 B1 | 7/2016 | Pathirage et al. |
| 9,468,541 B2 | 10/2016 | Contreras-Vidal et al. |
| 9,532,748 B2 | 1/2017 | Denison et al. |
| 9,563,273 B2 | 2/2017 | Mann |
| 9,629,976 B1* | 4/2017 | Acton ................. A61H 5/00 |
| 9,743,002 B2 | 8/2017 | Wierich |
| 10,664,050 B2 | 5/2020 | Alcaide et al. |
| 11,266,342 B2 | 3/2022 | Huggins et al. |
| 11,269,414 B2 | 3/2022 | Alcaide et al. |
| 11,366,517 B2 | 6/2022 | Alcaide et al. |
| 2002/0036381 A1 | 3/2002 | Scibetta |
| 2002/0065851 A1 | 5/2002 | Watson et al. |
| 2003/0031457 A1 | 2/2003 | Miomo et al. |
| 2003/0195798 A1 | 10/2003 | Goci |
| 2003/0203342 A1 | 10/2003 | Bowers |
| 2004/0043372 A1 | 3/2004 | Jebb et al. |
| 2004/0092809 A1 | 5/2004 | DeCharms |
| 2004/0169673 A1 | 9/2004 | Crampe et al. |
| 2004/0249302 A1 | 12/2004 | Donoghue et al. |
| 2005/0017870 A1 | 1/2005 | Allison et al. |
| 2005/0046698 A1 | 3/2005 | Knight |
| 2005/0085744 A1 | 4/2005 | Beverina et al. |
| 2005/0131311 A1 | 6/2005 | Leuthardt et al. |
| 2005/0170325 A1 | 8/2005 | Steinberg et al. |
| 2005/0191609 A1 | 9/2005 | Fadel et al. |
| 2005/0222873 A1 | 10/2005 | Nephin et al. |
| 2005/0226505 A1 | 10/2005 | Wilson |
| 2006/0093998 A1 | 5/2006 | Vertegaal |
| 2007/0066914 A1 | 3/2007 | Le et al. |
| 2007/0086773 A1 | 4/2007 | Ramsten et al. |
| 2007/0166675 A1 | 7/2007 | Atkins et al. |
| 2007/0166686 A1 | 7/2007 | Foster |
| 2007/0173733 A1 | 7/2007 | Le et al. |
| 2007/0179396 A1 | 8/2007 | Le et al. |
| 2008/0024724 A1 | 1/2008 | Todd |
| 2008/0065468 A1 | 3/2008 | Berg et al. |
| 2008/0218472 A1 | 9/2008 | Breen et al. |
| 2008/0228242 A1 | 9/2008 | Fink et al. |
| 2008/0317206 A1 | 12/2008 | Yoshino |
| 2009/0082692 A1 | 3/2009 | Hale et al. |
| 2009/0099623 A1 | 4/2009 | Bentwich |
| 2009/0125849 A1 | 5/2009 | Bouvin et al. |
| 2009/0175540 A1 | 7/2009 | Dariush et al. |
| 2009/0289895 A1 | 11/2009 | Nakada et al. |
| 2009/0319058 A1 | 12/2009 | Rovaglio et al. |
| 2010/0010391 A1 | 1/2010 | Skelton et al. |
| 2010/0039438 A1 | 2/2010 | Kennedy |
| 2010/0100001 A1 | 4/2010 | Aguilar et al. |
| 2010/0145215 A1 | 6/2010 | Pradeep et al. |
| 2010/0191140 A1 | 7/2010 | Terada et al. |
| 2010/0223549 A1* | 9/2010 | Edwards .......... H04N 21/42225 |
| | | 715/708 |
| 2010/0240016 A1 | 9/2010 | Ween et al. |
| 2010/0280403 A1 | 11/2010 | Erdogmus et al. |
| 2010/0317988 A1 | 12/2010 | Terada et al. |
| 2011/0004089 A1 | 1/2011 | Chou |
| 2011/0148927 A1 | 6/2011 | Tainsh et al. |
| 2011/0152710 A1 | 6/2011 | Kim et al. |
| 2011/0159467 A1 | 6/2011 | Peot et al. |
| 2011/0175932 A1 | 7/2011 | Yu et al. |
| 2011/0301486 A1 | 12/2011 | Van Hek et al. |
| 2012/0019662 A1 | 1/2012 | Maltz |
| 2012/0034583 A1 | 2/2012 | Dujowich et al. |
| 2012/0036097 A1 | 2/2012 | Prokhorov |
| 2012/0044154 A1 | 2/2012 | Black et al. |
| 2012/0150545 A1 | 6/2012 | Simon |
| 2012/0254745 A1 | 10/2012 | Sangiovanni et al. |
| 2012/0287284 A1 | 11/2012 | Jacobsen et al. |
| 2012/0289854 A1 | 11/2012 | Yamada et al. |
| 2012/0296476 A1 | 11/2012 | Cale et al. |
| 2013/0050432 A1 | 2/2013 | Perez et al. |
| 2013/0125027 A1 | 5/2013 | Abovitz |
| 2013/0130799 A1 | 5/2013 | Van Hulle et al. |
| 2013/0169560 A1 | 7/2013 | Cederlund et al. |
| 2013/0335573 A1 | 12/2013 | Forutanpour et al. |
| 2014/0058528 A1 | 2/2014 | Contreras-Vidal et al. |
| 2014/0065594 A1 | 3/2014 | Venable |
| 2014/0096077 A1* | 4/2014 | Jacob ................. G06F 3/013 |
| | | 715/810 |
| 2014/0223462 A1 | 8/2014 | Aimone et al. |
| 2014/0225918 A1 | 8/2014 | Mittal et al. |
| 2014/0228701 A1 | 8/2014 | Chizeck et al. |
| 2014/0247232 A1 | 9/2014 | George-Svahn et al. |
| 2014/0316230 A1 | 10/2014 | Denison et al. |
| 2014/0320397 A1 | 10/2014 | Hennessey et al. |
| 2014/0320817 A1 | 10/2014 | Kiderman et al. |
| 2014/0347265 A1 | 11/2014 | Aimone et al. |
| 2014/0372957 A1 | 12/2014 | Keane et al. |
| 2015/0042558 A1 | 2/2015 | Massonneau et al. |
| 2015/0199010 A1 | 7/2015 | Coleman et al. |
| 2015/0212576 A1 | 7/2015 | Ambrus et al. |
| 2015/0212695 A1 | 7/2015 | Nordstrom et al. |
| 2015/0338915 A1 | 11/2015 | Publicover et al. |
| 2016/0077547 A1 | 3/2016 | Aimone et al. |
| 2016/0103484 A1 | 4/2016 | Guo et al. |
| 2016/0187976 A1 | 6/2016 | Levesque et al. |
| 2016/0198091 A1 | 7/2016 | Edwards |
| 2016/0235323 A1 | 8/2016 | Tadi et al. |
| 2016/0253890 A1 | 9/2016 | Rabinowitz et al. |
| 2016/0259519 A1 | 9/2016 | Foss et al. |
| 2016/0259528 A1 | 9/2016 | Foss et al. |
| 2017/0078447 A1 | 3/2017 | Hancock et al. |
| 2017/0124928 A1 | 5/2017 | Edwin et al. |
| 2017/0139556 A1* | 5/2017 | Josephson ........... H04L 12/2803 |
| 2017/0188933 A1 | 7/2017 | Huggins et al. |
| 2017/0249009 A1* | 8/2017 | Parshionikar ........... G06F 3/012 |
| 2017/0290504 A1 | 10/2017 | Khaderi et al. |
| 2017/0293356 A1 | 10/2017 | Khaderi et al. |
| 2017/0316707 A1 | 11/2017 | Lawrenson et al. |
| 2017/0322679 A1* | 11/2017 | Gordon ................. G06N 20/00 |
| 2017/0323615 A1 | 11/2017 | Hazra et al. |
| 2018/0008141 A1 | 1/2018 | Krueger |
| 2018/0039329 A1 | 2/2018 | Tumey |

(56) References Cited

U.S. PATENT DOCUMENTS

| | | |
|---|---|---|
| 2018/0321739 A1 | 11/2018 | Park |
| 2018/0364810 A1 | 12/2018 | Parshionikar |
| 2019/0246982 A1 | 8/2019 | Mackellar et al. |
| 2019/0286234 A1 | 9/2019 | Condolo |
| 2020/0337653 A1 | 10/2020 | Alcaide et al. |
| 2021/0113129 A1 | 4/2021 | Huang |
| 2021/0141453 A1 | 5/2021 | Miller, III |
| 2022/0404910 A1 | 12/2022 | Alcaide et al. |
| 2023/0107040 A1 | 4/2023 | Alcaide et al. |

FOREIGN PATENT DOCUMENTS

| | | |
|---|---|---|
| CN | 101339455 A | 1/2009 |
| CN | 101515199 A | 8/2009 |
| CN | 101515199 B | 1/2011 |
| CN | 102098639 A | 6/2011 |
| CN | 103092340 A | 5/2013 |
| CN | 103421859 A | 12/2013 |
| CN | 103793058 A | 5/2014 |
| CN | 103955269 A | 7/2014 |
| CN | 104837088 A | 8/2015 |
| CN | 105051647 A | 11/2015 |
| CN | 107072583 A | 8/2017 |
| EP | 2613222 A1 | 7/2013 |
| JP | H10260773 A | 9/1998 |
| JP | H1165794 A | 3/1999 |
| JP | 2002236957 A | 8/2002 |
| JP | 2003058298 A | 2/2003 |
| JP | 2010015584 A | 1/2010 |
| JP | 4465414 B2 | 5/2010 |
| JP | 2010218491 A | 9/2010 |
| JP | 2012053656 A | 3/2012 |
| JP | 2012221498 A | 11/2012 |
| JP | 2013004006 A | 1/2013 |
| JP | 2013190942 A | 9/2013 |
| JP | 2013244116 A | 12/2013 |
| JP | 2016126773 A | 7/2016 |
| JP | 2016207115 A | 12/2016 |
| JP | 2017058971 A | 3/2017 |
| JP | 2018505457 A | 2/2018 |
| JP | 2018529171 A | 10/2018 |
| JP | 2020503906 A | 2/2020 |
| KR | 101023249 B1 | 3/2011 |
| KR | 20150081846 A | 7/2015 |
| KR | 10-2015-0140286 A | 12/2015 |
| KR | 101579364 B1 | 12/2015 |
| KR | 10-2016-0061699 A | 6/2016 |
| KR | 10-1723841 B1 | 4/2017 |
| RU | 2627075 C1 | 8/2017 |
| WO | WO-02091119 A2 | 11/2002 |
| WO | WO-03037231 A1 | 5/2003 |
| WO | WO-2004073485 A2 | 9/2004 |
| WO | WO-2005079332 A2 | 9/2005 |
| WO | WO-2006051709 A1 | 5/2006 |
| WO | WO-2007044431 A2 | 4/2007 |
| WO | WO-2007086222 A1 | 8/2007 |
| WO | WO-2009056650 A1 | 5/2009 |
| WO | WO-2009089532 A1 | 7/2009 |
| WO | WO-2009093435 A1 | 7/2009 |
| WO | WO-2009139119 A1 | 11/2009 |
| WO | WO-2010147913 A1 | 12/2010 |
| WO | WO-2011105000 A1 | 9/2011 |
| WO | WO-2011140303 A1 | 11/2011 |
| WO | WO-2012020906 A1 | 2/2012 |
| WO | WO-2012071544 A2 | 5/2012 |
| WO | WO-2012137801 A1 | 10/2012 |
| WO | WO-2013012739 A1 | 1/2013 |
| WO | WO-2014116826 A1 | 7/2014 |
| WO | WO 2014/144940 A2 | 9/2014 |
| WO | WO-2016064314 A1 | 4/2016 |
| WO | WO-2016073131 A1 | 5/2016 |
| WO | WO-2016193979 A1 | 12/2016 |
| WO | WO-2017031089 A1 | 2/2017 |
| WO | WO-2017046698 A1 | 3/2017 |
| WO | WO-2017104869 A1 | 6/2017 |
| WO | WO-2018064627 A1 | 4/2018 |
| WO | WO-2018127782 A1 | 7/2018 |

OTHER PUBLICATIONS

Aref, A. W., "The P300-Certainty Algorithm: Improving accuracy by withholding erroneous selections," ECNS Conference, Bristol, Tennessee, Sep. 12-16, 2012, p. 79.

Bai, O. et al., "Exploration of computational methods for classification of movement intention during human voluntary movement from single trial EEG," Clin. Neurophysiol., 118:2637-2655 (2007).

Bai, O. et al., "Towards a User-Friendly Brain-Computer Interface: Initial Tests in ALS and PLS Patients," Clin. Neurophysiol., 121:1293-1303 (2010).

Bashashati, A. et al., "A survey of signal processing algorithms in brain-computer interfaces based on electrical brain signals," J. Neural. Eng., 4:R32-R57 (2007).

Cipresso, P. et al., "The combined use of Brain Computer Interface and Eye-Tracking technology for cognitive assessment in Amyotrophic Lateral Sclerosis," 2011 5th International Conference on Pervasive Computing Technologies for Healthcare and Workshops, Pervasive Health 2011, 5 pages.

Cipresso, P. et al., "The use of P300based BCIs in amyotrophic lateral sclerosis: from augmentative and alternative communication to cognitive assessment," Brain and Behavior, 2(4):479-498 (2012).

Communication pursuant to Article 94(3) dated Jan. 25, 2023 for European Application No. 18848298.8, 9 pages.

Connolly, J. F. & D'Arcy, R. C., "Innovations in neuropsychological assessment using event-related brain potentials," Int. J. Psychophysiol., 37:31-47 (2000).

Connolly, J. F. et al., "Performance on WISC-III and WAIS-R NI vocabulary subtests assessed with event-related brain potentials: an innovative method of assessment," J. Clin. Exp. Neurophsychol., 21:444-464 (2010).

D'Arcy, R. C. et al., "Electrophysiological assessment of language function following stroke," Clin. Neurophysiol., 114:662-672 (2003).

D'Arcy, R. C. et al., "Evaluation of reading comprehension with neuropsychological and event-related brain potential (ERP) methods," J. Int. Neurophyschol. Soc., 6(5):556-567 (2000).

Extended European Search Report dated Apr. 19, 2018 for European Application No. 15799099.5, 13 pages.

Extended European Search Report dated Apr. 19, 2021 for European Application No. 18848298.8, 15 pages.

Extended European Search Report dated Apr. 28, 2022 for European Application No. 19861902.5, 7 pages.

Extended European Search Report dated Jan. 24, 2022 for European Application No. 19741853.6, 12 pages.

Extended European Search Report dated Jul. 14, 2021 for European Application No. 18875541.7, 10 pages.

Final Office Action mailed Mar. 12, 2021 for U.S. Appl. No. 15/305,030, 13 pages.

Hampshire, A. et al., "Assessing residual reasoning ability in overtly non-communicative patients using fMRI," Neuroimage: Clinical, 2:174-183 (2012).

Heun, V. et al., "Smarter Objects: Using AR technology to Program Physical Objects and their Interactions," CH 2013 Extended Abstracts, Apr. 27-May 2, 2013, pp. 961-966 (2013).

International Search Report and Written Opinion mailed Aug. 31, 2015 for International Application No. PCT/2015/032192, 9 pages.

International Search Report and Written Opinion mailed Dec. 18, 2019 for International Application No. PCT/US19/51997, 20 pages.

International Search Report and Written Opinion mailed Jan. 22, 2019 for International Application No. PCT/US2018/060797, 10 pages.

International Search Report and Written Opinion mailed Jun. 20, 2019 for International Application No. PCT/US19/14315, 16 pages.

International Search Report and Written Opinion mailed Oct. 22, 2018 for International Application No. PCT/US2018/047598, 17 pages.

(56) References Cited

OTHER PUBLICATIONS

Iverson, I. H. et al., "A brain-computer interface tool to assess cognitive functions in completely paralyzed patients with amyotrophic lateral sclerosis," Clin. Neurophysiol., 119:2214-2223 (2008).
Jiang, J., et al., "Hybrid Brain-Computer Interface (BCI) based on the EEG and EOG signals, Bio-Medical Materials and Engineering," 2014, vol. 24, No. 6, pp. 2919-2925, [Online; retrieval date: Jan. 24, 2023], Internet, URL: https://content.iospress.com/articles/bio-medical-materialsand-engineering/bme1111, DOI:10.3233/BME-141111.
Kübler, A. et al., "Brain-Computer Interfaces and communication in paralysis: extinction of goal directed thinking in completely paralysed patients?" Clin. Neurophysiol., 119:2658-2666 (2008).
Makeig, S. et al., "Evolving Signal Processing for Brain-Computer Interfaces," Proc. of the IEEE, 100:1567-1584 (2012).
Martens, S. M. M. et al., "Overlap and refractory effects in a brain-computer interface speller based on the visual P300 event related potential; Overlap and refractory effects in a BCI speller based on the visual P300 ERP," Journal of Neural Engineering, 6(2):1741-2552 (2009).
Mohsenzadeh, Y. et al., "A State Space Model for Spatial Updating of Remembered Visual Targets during Eye Movements," Frontiers in Systems Neuroscience, vol. 10, May 12, 2016; 10:39, 22 pages; doi:10.3389/fnsys.2016.00039.
Murguialday, R. A. et al., "Brain-Computer Interface for a Prosthetic Hand Using Local Machine Control and Haptic Feedback," 10th International Conference on Rehabilitation Robotics, IEEE, pp. 609-613 (2007).
Naci, L. et al., "Brain-Computer Interfaces for Communication with Nonresponsive Patients," Ann. Neurol., 72:312-323 (2012).
Nishino, S., et al., Abstract "A Basic Study on Speeding up Japanese Input BCI with Linguistic Feature, IEICE Technical Report AI2016-1-AI2016-11, Artificial Intelligence and Knowledge-Based Processing", Japan, The Institute of Electronics, Information and Communication Engineers, vol. 116, No. 117, Jun. 20, 2016, 4 pages.
Non-Final Office Action for U.S. Appl. No. 17/747,735 dated Jul. 3, 2023, 13 pages.
Non-Final Office Action mailed Aug. 15, 2019 for U.S. Appl. No. 16/138,791, 12 pages.
Non-Final Office Action mailed Aug. 31, 2021 for U.S. Appl. No. 15/305,030, 17 pages.
Non-Final Office Action mailed Jan. 13, 2020 for U.S. Appl. No. 15/305,030, 12 pages.
Non-Final Office Action mailed Jan. 25, 2023 for U.S. Appl. No. 17/589,175, 16 pages.
Non-Final Office Action mailed Jul. 28, 2021 for U.S. Appl. No. 16/847,020, 14 pages.
Non-Final Office Action mailed Jun. 12, 2019 for U.S. Appl. No. 15/305,030, 10 pages.
Non-Final Office Action mailed Nov. 19, 2020 for U.S. Appl. No. 15/305,030, 13 pages.
Non-Final Office Action mailed Apr. 14, 2021 for U.S. Appl. No. 16/797,376, 18 pages.
Notice of Reasons for Rejection dated Apr. 25, 2023 for Japanese Application No. JP20200532856, with English translation, 11 pages.
Notice of Reasons for Rejection mailed Aug. 2, 2022 for Japanese Application No. JP20200532856, with translation, 9 pages.
Office Action and Search Report for Chinese Application No. CN20188069216 dated Mar. 4, 2023, with English translation, 20 pages.
Office Action and Search report for Chinese Application No. CN20188085323 mailed Feb. 15, 2023, with English translation, 34 pages.
Office Action for European Application No. 18875541.7 dated May 9, 2023, 5 pages.
Office Action for Japanese Application No. JP20200537522 dated Jan. 26, 2023, with English translation, 11 pages.
Office Action for Japanese Application No. JP2020544378 dated Dec. 2, 2022, 10 pages, with English translation, 10 pages.
Partial Supplementary European Search Report dated Jan. 3, 2018 for European Application No. 15799099.5, 13 pages.
Partial Supplementary European Search Report dated Oct. 15, 2021 for European Application No. 19741853.6, 14 pages.
Perego, P. et al., "Cognitive ability assessment by Brain-Computer Interface: Validation of a new assessment method for cognitive abilities," J. Neurosci. Methods, 201:239-250 (2011).
Power, D. et al., "Towards a system-paced near-infrared spectroscopy braincomputer interface: differentiating prefontal activity due to mental arithmetic and mental singing from the no-control state; Towards a system-paced near-infrared spectroscopy brain-computer interface," Journal of Neural Engineering, 8(6):66004 (2011), 14 pages, doi:10.1088/1741-2560/8/6/066004.
Sakai, Y., et al., Abstract, "A study on the relationship between gazing points and event-related potentials for a P300-based brain computer interface, IEICE Technical Report MBE2012-30-MBE2012-35, ME and Bio Cybernetics", Japan, The Institute of Electronics, Information and Communication Engineers, vol. 112, No. 220, Sep. 20, 2012, 4 pages.
Sellers, E. W. & Donchin, E., "A P300-based brain-computer interface: initial tests by ALS patients," Clin. Neurophysiol., 117:528-548 (2006).
Seo, S. et al., "Discrimination of Yes and No Responses by Auditory Stimuli Multiple-choice Questions in Human EEG," International Conference on Convergence Information Technology, IEEE, pp. 1127-1133 (2007).
Sorger, B. et al., "Another kind of 'BOLD Response': answering multiple-choice questions via online decoded single-trial brain signals," Progress in Brain Research, Chapter 19, vol. 177, pp. 275-292 (2009).
Thompson, D. E. et al., "Classifier-based latency estimation: a novel way to estimate and predict BCI accuracy," J. Neural Eng., 10(1):016006 (2013), 13 pages, doi:10.1088/1741-2560/10/1/016006. Epub Dec. 12, 2012.
Thompson, D. E. et al., "Performance assessment in brain-computer interface-based augmentative and alternative communication," BioMedical Engineering Online, 12:43 (2013), 23 pages, doi:10.1186/1475-925X-12-43.
Vieru, T., "Brain Computer Interface Can Stimulate the Cortex," Softpedia (Feb. 16, 2010), 4 pages.
Zander, T. O. & Kothe, C., "Towards passive brain-computer interfaces: applying brain-computer interface technology to human-machine systems in general," J. Neural Eng., 8(2):025005 (2011), 5 pages, doi:10.1088/1741-2560/8/2/025005. Epub Mar. 24, 2011.
Communication pursuant to Article 94(3) for European Application No. EP18875541.7 dated Feb. 2, 2024, 5 pages.
Communication pursuant to Article 94(3) for European Application No. 19861902.5 dated Jan. 23, 2024, 5 pages.
Examination Report dated Oct. 4, 2023 for European Application No. 19741853.6, 5 pages.
Final Notice of Reasons for Rejection dated Sep. 20, 2023 for Japanese Application No. 2020-544378, with English translation, 11 pages.
Final Notice of Reasons for Rejection for Japanese Application No. JP20200532856 dated Jan. 23, 2024, with English translation, 5 pages.
Non-Final Office Action for U.S. Appl. No. 16/926,331 dated Sep. 22, 2023, 26 pages.
Notice of Preliminary Rejection for Korean Application No. KR1020207008357 dated Sep. 27, 2023, with English translation, 18 pages.
Office Action and Search report for Chinese Application No. CN201880069216 dated Dec. 11, 2023, with English translation, 10 pages.
Office Action and Search Report for Chinese Application No. CN201880085323 dated Jan. 16, 2024, with English translation, 10 pages.
Office Action and Search Report for Chinese Application No. CN201980071792.2 dated Sep. 21, 2023, with English translation, 29 pages.
Office Action and Search Report for Chinese Application No. CN20198013115 dated Jul. 17, 2023, with English translation, 25 pages.

(56) References Cited

OTHER PUBLICATIONS

Office Action for Japanese Application No. JP20200537522 dated Oct. 24, 2023, with English translation, 9 pages.
Office Action for Japanese Application No. JP2021515495 mailed Oct. 17, 2023, with machine translation, 9 pages.

* cited by examiner $T_0$: Object appears. motion noticed
$T_1$: Object Tracking. Dynamic Tag assigned/placed
$T_2$: Tag flash on object
$T_3$: Motion Continues
$T_4$: Tag flash on object
$T_5$: End of object tracking

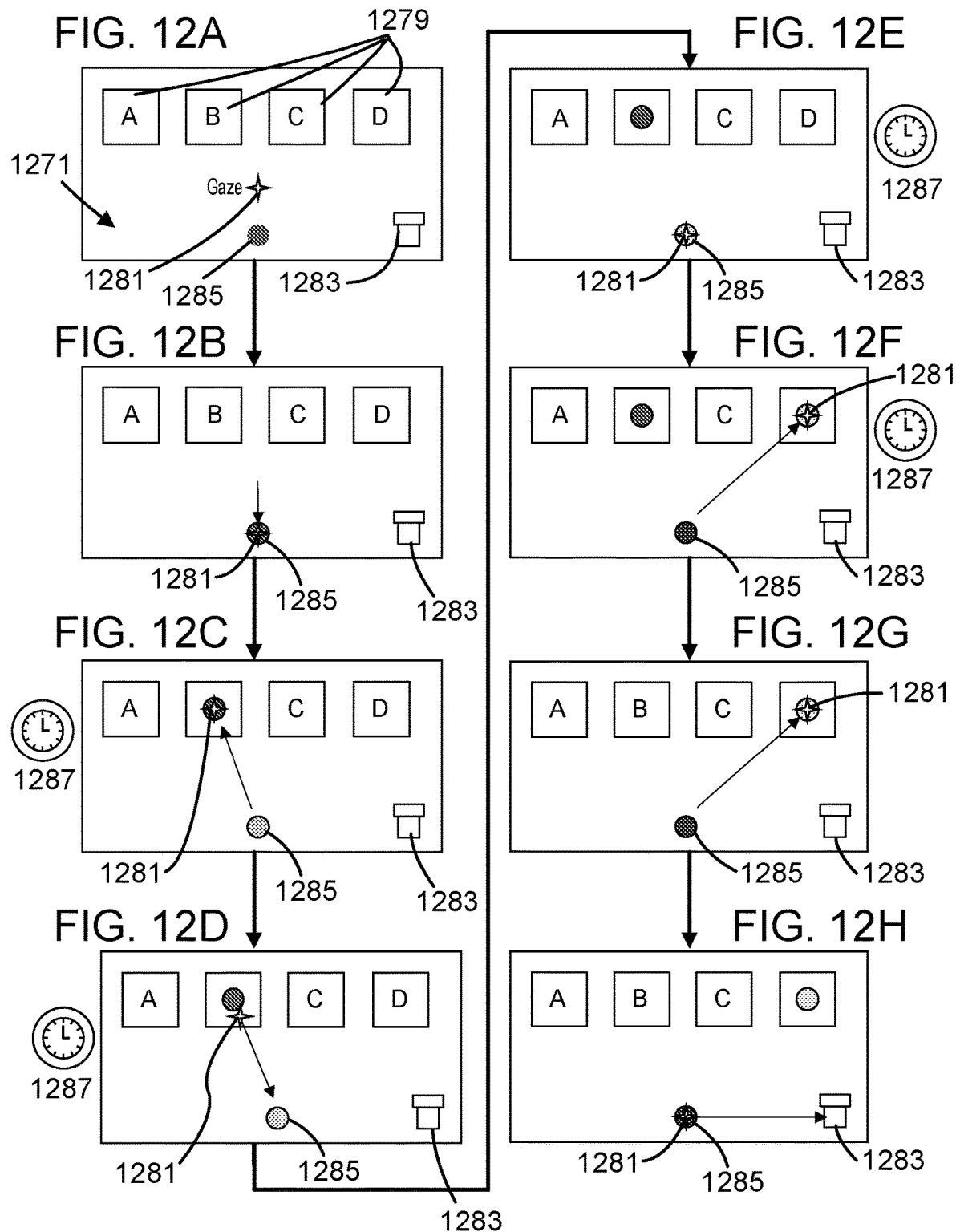

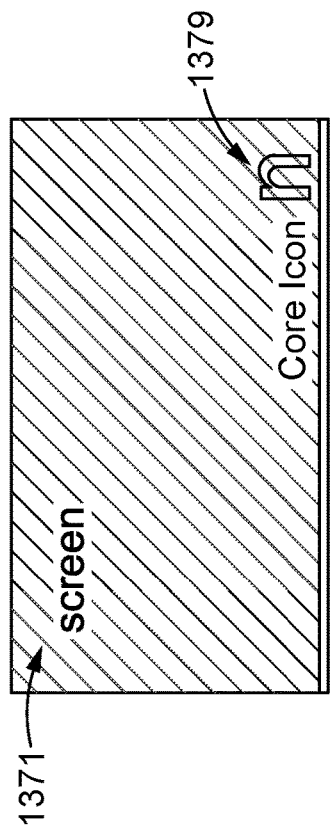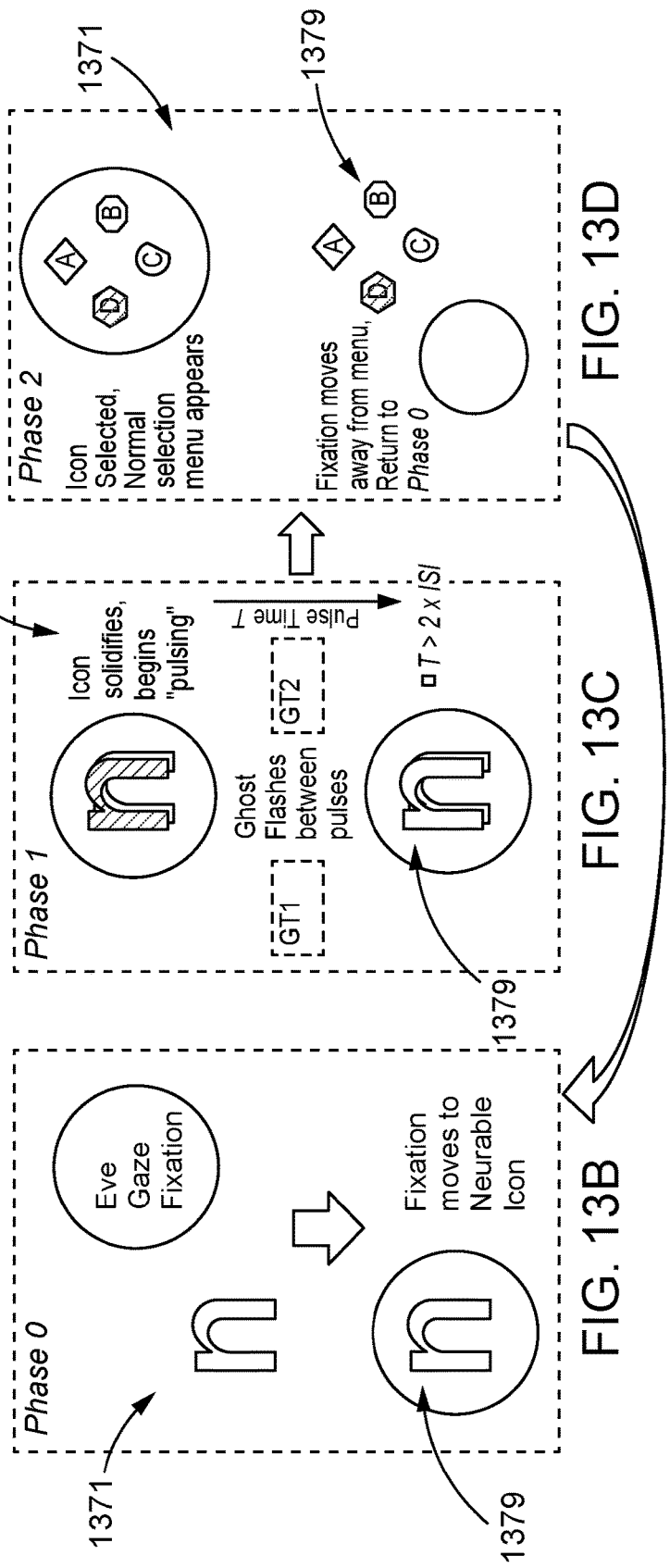

BRAIN-COMPUTER INTERFACE WITH ADAPTATIONS FOR HIGH-SPEED, ACCURATE, AND INTUITIVE USER INTERACTIONS

CROSS-REFERENCE TO RELATED APPLICATIONS

This application is a continuation of International Patent Application No. PCT/US2018/060797, filed Nov. 13, 2018, and titled "BRAIN-COMPUTER INTERFACE WITH ADAPTATIONS FOR HIGH-SPEED, ACCURATE, AND INTUITIVE USER INTERACTIONS," which claims priority to and the benefit of U.S. Provisional Patent Application Ser. No. 62/585,209, entitled "Brain-Computer Interface with Adaptations for High-Speed, Accurate, and Intuitive User Interactions," filed Nov. 13, 2017, the disclosures of which are hereby incorporated by reference in their entirety.

BACKGROUND

Embodiments described herein relate to systems, devices, and methods for use in the implementation of a brain-computer interface that uses brain activity tracking to present and update a user interface (UI) or a UX that is strategically designed for high speed and accuracy of human-machine interaction, to mediate user manipulation of machines. Embodiments described herein also relate to the implementation of a hardware agnostic brain-computer interface that integrates eye-movement tracking and the analysis of neural activity to mediate user manipulation of machines.

A brain-computer interface (BCI) is a hardware and software communications system that permits brain activity alone to control computers or external devices with direct communication pathways between a wired brain and the external device. BCIs have been mainly designed as an assistive technology to provide access to operating machines and applications directly from interpreting brain signals. One of the main goals of BCI development is to provide communication capabilities to severely disabled people who are totally paralyzed or 'locked in' by neurological neuromuscular disorders, such as amyotrophic lateral sclerosis, brainstem stroke, or spinal cord injury, for whom effective communication with others may be extremely difficult.

Some known implementations of brain computer interfaces include spellers like the one designed by Farwell and Donchin. In this speller, the 26 letters of the alphabet, together with several other symbols and commands, are displayed on-screen in a 6×6 matrix with randomly flashing rows and columns. The user focuses attention on the screen and concentrates successively on the characters to be written, while the neural response of the brain is monitored for signature neural brain signals. Once detected the signature brain signals allow the system to identify the desired symbol. The Farwell-Donchin speller allows people to spell at the rate of about 2 characters per minute.

BCI systems can be designed to assist and enhance even physically able people to operate computers or other data-processing machines and/or software applications without the need for conventional input or output interfaces such as a mouse and a keyboard. BCIs may also provide an interface for more intuitive and natural interaction with a computer than conventional input methods. Additionally, BCIs can also be developed to serve many other functions including augmenting, repairing as well as mapping and researching human and animal cognitive and/or sensory motor systems and their functions. Some BCI applications include word processors, adapted web browsers, brain control of a wheelchair or neuroprostheses, and games, among others.

SUMMARY

Systems, devices and methods are described herein for various embodiments of a hardware-agnostic, integrated oculomotor-neural hybrid brain computer interface (BCI) platform to track eye movements and brain activity to mediate real-time positioning of a user's gaze or attention and selection/activation of desired action. This disclosure presents an integrated hybrid BCI system to address the need for Brain Computer Interfaces that operate with high-speed and accuracy.

BRIEF DESCRIPTION OF THE FIGURES

FIGS. 12A-12H show illustrations of a UI of a hybrid BCI system, implementing an example use of a draggable sticky marker, according to an embodiment.

FIG. 13A shows an example UI implementing an adaptation for user interaction, according to an embodiment.

FIG. 13B-13D illustrate the mechanism of implementing a UI adaptation of selection activation, according to an embodiment.

DETAILED DESCRIPTION

Figure 1:
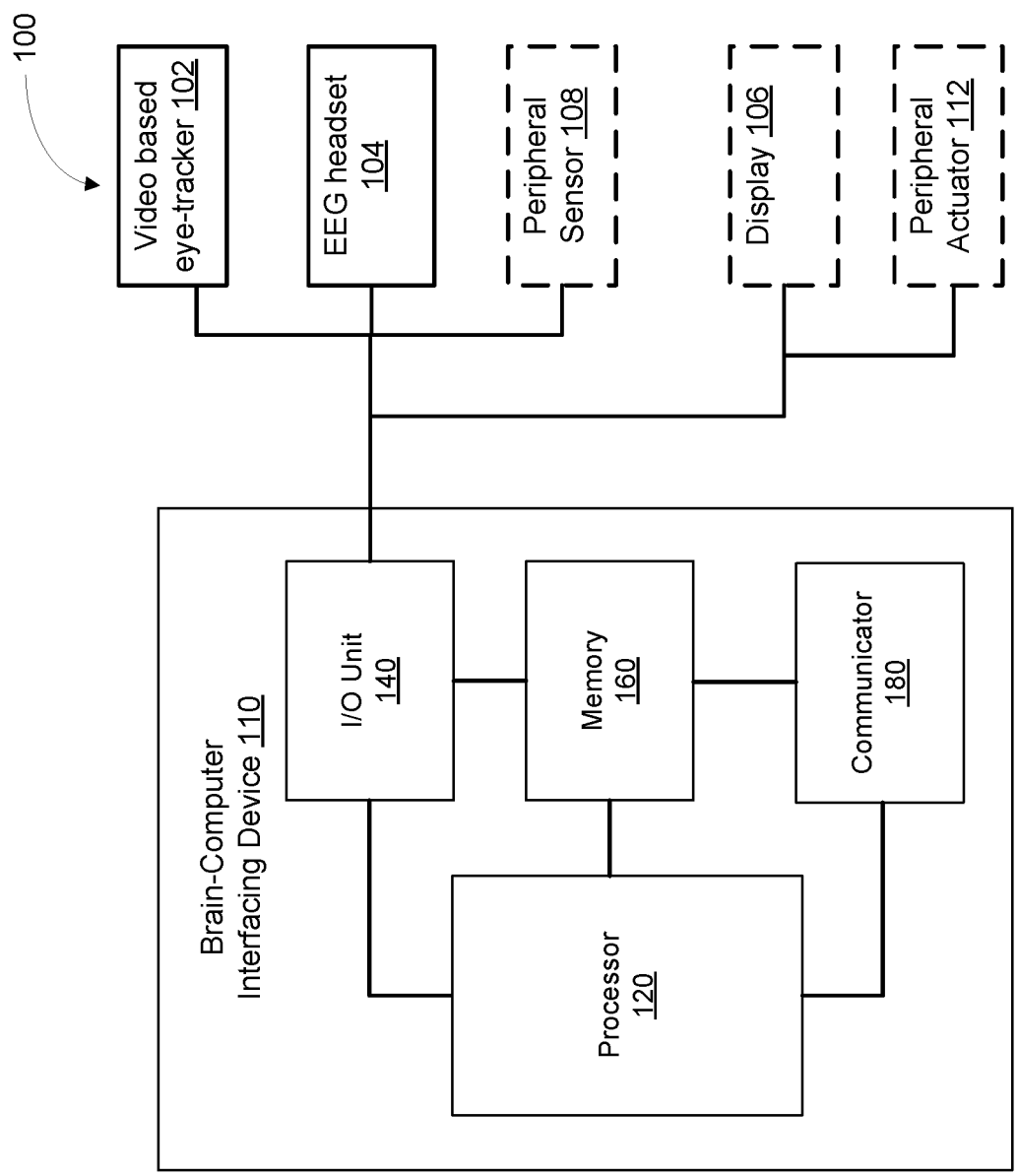
FIG. 1 is a schematic illustration of a hybrid Brain Computer Interfacing system, according to an embodiment.

Embodiments described herein relate to systems, devices, and methods for use in the implementation of a hybrid brain-computer interface (BCI) that integrates real-time eye-movement tracking with brain activity tracking to present and update a UI that is strategically designed for high speed and accuracy of human-machine interaction. Embodiments described herein also relate to the implementation of a hardware agnostic brain-computer interface that uses real-time eye tracking and online analysis of neural brain signals to mediate user manipulation of machines.

For BCI technology to be better suited for patients, useful to the general public, and employed in the control of real-world tasks, the information transfer rate has to be improved to meet a natural interactive pace, the error rate has to be reduced, and the complexity of the interaction interface has to be minimized, compared to current implementations. Additionally, BCI applications demand a high cognitive load from the users, thus the UI has to be improved to move away from quiet laboratory environments into the real world. In order to configure BCI devices and applications to be easier and more intuitive, there exists a need for improved devices and techniques in the implementation of brain machine interfaces that operate with high-speed and high accuracy to enable user mediated action selection through a natural intuitive process.

A Hybrid BCI System

As described herein, a BCI is a hardware and software communications system that permits brain activity alone to control computers or external devices. A hybrid BCI system includes a display of stimuli through an interface, a hardware apparatus to locate the point of focus of a user on the interface, a device for recording and processing brain activity, and an apparatus for effecting control of the interface, which may translate into control over the user's environment. These standard features can be characterized as (1) a pointing control feature, (2) an action control feature, and (3) a UI feature. The pointing control feature can be analogized to a conventional pointing device like a mouse pointer that allows a user to narrow down to a small set of one or more manipulators to control. The action control feature can be analogized to a selection device, for example a mouse click or a key stroke on a keyboard, that allows the user to implement an action to effect change to the UI and in turn to a connected machine. The UI feature in a hybrid BCI system can be analogized to an operating system that creates and maintains an environment that implements the pointing and action control features in addition to other features like offering a selection menu, navigation controls, etc.

The action performed by the action control feature can be one of many and can be adapted to suit various versions of UIs designed to control various devices or machines. To name a few examples, the action can be an activation or a deactivation, a continuous or semi-continuous change to the UI (e.g., scrolling, hovering, pinching, zooming, titling, rotating, swiping, etc.). The action can also effect an acute change to the UI with discrete starts and stops like highlighting, etc. Some other examples of action control via a UI can include a virtual keyboard control, menu navigation, actions to place and unplace object or items, action to move objects or items, expand and/or shrink objects, movement or navigation of a first-person observer or player, changing perspectives of the observer, and actions like grabbing, picking or hovering. Some of these aspects of action control are disclosed below.

In some embodiments of a hybrid BCI system described herein, the pointing control feature and methods for identifying a user's point of focus can include an eye-tracking device. In some embodiments, the action control feature and methods for identifying the intent of the user can include any suitable form of monitoring neural signals in the brain. This can include any form of recording brain activity, for example, brain imaging methods like electrical, optical or magnetic imaging. For example, in some embodiments, the hybrid BCI system can use electrodes recording neural signals of brain activity, channeled through an amplifier and a processor that convert the user's brain signals to BCI commands. In some embodiments, the hybrid BCI systems can implement sophisticated UIs that implement brain activity based control of machines. Specific adaptations to one or more of these features can be implemented, as described below, to achieve high speed and accuracy of human interaction with the hybrid BCI system. For example, in some embodiments, the hybrid BCI system can be substantially similar to those described in U.S. Patent Application No. 62/549,253, entitled, "Brain-computer interface with high-speed eye tracking features," filed Aug. 25, 2017 ("the '253 application"); International Patent Application No. PCT/US2018/047598, entitled, "Brain-computer interface with high-speed eye tracking features," filed Aug. 22, 2018, which claims priority to the '253 application; and U.S. patent application Ser. No. 16/138,791, entitled, "Brain-computer interface using high-speed and accurate tracking of user interactions," filed Sep. 21, 2018. The disclosure(s) of each of these applications is incorporated herein by reference in its entirety.

FIG. 1 is a schematic illustration of a hybrid Brain Computer Interface system 100, according to an embodiment. The example hybrid Brain Computer Interface system 100 (also referred to herein as "hybrid BCI system" or "BCI system" or "system") is an integrated oculomotor-neural hybrid BCI system that includes an eye-tracker 102 (e.g., a video based eye-tracker) and a neural recording headset 104 for recording one or more control signals of the user's brain. The hybrid BCI system can optionally also include an electromyograph (EMG) to record EMG signals that can be integrated in with the oculomotor-neural hybrid. The video based eye-tracker 102 can be configured to capture, record, and transmit oculomotor responses of the eyes of a user 102 indicating the user's point of focus at any time (i.e., the pointing control feature). The neural recording headset 104 can be configured to capture, record and transmit neural control signals from one or more brain regions indicating the user's cognitive intent (i.e., the action control feature). The neural control signals can be any form of neural activity recorded through any suitable approach, for example, electroencephalography (EEG), electrocorticography (ECoG) or magnetoencephalography (MEG), etc. Example forms of neural activity include Event Related Potentials (ERPs), motor imagery, steady state visual evoked potentials (SSVEPs), transitory visual evoked potentials (TVEPs), brain state commands, visual evoked potentials (VEPs), evoked potentials like the P300 evoked potential, sensory evoked potentials, motor evoked potentials, sensorimotor rhythms such as the mu rhythm or beta rhythm, event related desynchronization (ERDs), event-related synchronization (ERSs), slow cortical potentials (SCPs), etc. The example hybrid BCI system 100 also includes a Brain-Computer Interfacing Device 110, and optionally an audio-visual display 106.

In some embodiments of the hybrid BCI system 100, the collected neural and oculomotor data can be communicated to the Brain-Computer Interfacing Device 110 that processes the signals as an ensemble along with data about what stimuli were presented. With the combined information, the Brain-Computer interfacing Device 110 can detect relevant signal features based on statistical models to predict the user's intent. This predicted intent can then be communicated to the user, via the UI presented through the display 106 for example, and used to effect change in the UI and in any connected controllable machine. Some embodiments of the hybrid BCI system 100, can also include other peripheral sensors and actuators (not shown in FIG. 1) to collect data about the users behavior thought other modalities like sound, touch, orientation, etc. and to present a rich, multimodal, UX.

Eye Tracking in Two and Three-Dimensional Space—the Pointing Control Feature

In some embodiments, the video based eye-tracker 102 can be used to determine where a user is looking in their visual field by rapidly following the eye movements of the user in a two or three-dimensional space. For example, provided the user has voluntary control of their eye-movements, the video based eye tracer 102 can be used to determine which subspaces in their visual field each of their eyes is "pointing to." In other words, the video based eye-tracker 102 can use the user's eye-movement trajectories as a pointing control feature, revealing significant information about the subject's intent and behavior. In some embodiments, aspects of where in the visual space their attention focused, what stimulus they are focused upon, or what stimulus they responded to, can be used effectively in the BCI system 100. By simultaneously tracking the movement trajectories of both eyes with respect to each other the video based eye-tracker 102 can also register the depth of focus of the user, thus enabling pointing control in a three-dimensional space.

In some embodiments, the video based eye-tracker 102 relies on tracking the user's pupil and a first-surface corneal reflection (CR) of an illumination source with the use of a head-mounted eye tracking video camera to image the user's eye. The positional difference between these two features can be used to determine the observer's eye-in-head orientation. Some example head mounted eye-tracking devices that can be used as the video based eye-tracker 102 are available from SenseMotoric Instruments, Tobii Eye Tracking, and Pupil-labs among other commercial vendors. In some embodiments, the video based eye-tracker 102 can include one or more illumination sources illuminating the eyes of a user. The illumination sources can be emitting light of any suitable wavelength and be mounted at any suitable position. The illumination sources can be connected through wired or wireless communication for function control and transmission of data, etc.

The video based eye-tracker 102 can include a left and a right eye camera configured to simultaneously image the pupil and the corneal reflection of the one or more illumination sources, from each eye. The cameras can be connected to each other, and can be connected to an external device like the Brain-Computer Interfacing (BCI) Device 110 shown in FIG. 1, through a wired or wireless connection. The video based eye-tracker can also include an additional scene camera that captures the user's field of view. The signals from the scene camera can also be relayed through wired or wireless communication methods to the external device like the BCI Device 110.

In some embodiments, the video based eye-tracker 102 can use a near infrared (IR) illumination source that is optimally reflected by the iris and is invisible to humans so it does not disturb or distract the user. The strong IR reflectance can yield high contrast images that are particularly beneficial to pupil detection. In some embodiments, the video based eye-tracker 102 can use a collimated, far range light source whereby parallel rays are emitted from a distant illumination source and collimated by optical components. In some embodiments, the video based eye-tracker 102 can use a non-collimated near-source for illuminating the eye whereby the illumination source is mounted at a finite distance (typically 50 mm or less) from the eye and there is no optical component between the source and the eye to collimate the rays.

As described herein, the video based eye-tracker 102 utilizes the light reflected from the eye, which is sensed by a video camera or some any other suitable optical sensor specially designed for this use. The sensed light is then analyzed to extract eye rotation from changes in reflections. In some embodiments, the video based eye-tracker 102 can use the corneal reflection (i.e., the first Purkinje image) and the center of the pupil as features to track over time. In some embodiments, the video based eye-tracker 102 can use reflections from the front of the cornea (i.e., the first Purkinje image) and the back of the lens (i.e., the fourth Purkinje image) as features to track eye movement in a more sensitive approach. In some embodiments, the video based eye-tracker 102 can use even more sensitive methods of tracking by imaging features inside the eye, such as, for example, the retinal blood vessels, and following the movement of these features as the eye rotates.

In some embodiments, the video based eye-tracker 102 can include an integrated display as described below. The video based eye-tracker 102 integrated with a display 106 can be a system configured to view virtual reality space. In some embodiments, the video based eye-tracker 102 integrated with a display 106 can be configured to view augmented reality space. In other words, functioning to view the real-world as a pair of eye-glasses with the addition of a superimposed UI presented through the display 106.

Neural Recording of Brain Signals—the Action Control Feature

The purpose of the hybrid BCI system 100 is to actively control external machines by interpreting user intentions from monitoring cerebral activity. Central to this purpose are brain signals that can be indicative of the user's intent, making the brain signals an action control feature. The hybrid BCI system 100 can use one or more of several signature brain signals simultaneously evoked by or related to cognitive tasks performed by a user. Some of these brain signals can be decoded in ways that people may learn to modulate them at will. Using these signals, regarded as control signals, can enable the hybrid BCI system 100 to interpret the intentions of the user.

Neural activity of electrophysiological origin is generated by electro-chemical transmitters exchanging information between the neurons. The neurons generate ionic currents which flow within and across neuronal assemblies. The large variety of current pathways can be simplified as a dipole conducting current from a source to a sink through the dendritic trunk. These intracellular currents are known as primary currents. Conservation of electric charges dictates that the primary currents are enclosed by extracellular current flows, which are known as secondary currents.

The neural recording headset 104 can be adapted to record neural activity following any suitable approach. Neural activity can be recorded either directly by electrically monitoring the primary currents or by electrically recording the secondary currents. Additionally, the neural activity can also be monitored through other methods like optical imaging (e.g. functional magnetic resonance imaging, fMRI), by the recording optical changes that are consequent to the primary currents. Other approaches to recording neural activity of the brain that can be used include electroencephalography (EEG), epidural and subdural electrocorticography (ECoG), Functional Near-Infrared Imaging and other similar Intrinsic Signal Imaging methods, magnetoencephalography (MEG), multi-electrode recordings, single-neuron intracortical recordings, etc.

A variety of signature brain signals in the form of neural activity can be used as a control signal used for implementing the action control feature. Some examples of neural activity in time include Event Related Potentials (ERPs), motor imagery, steady state visual evoked potentials (SSVEPs), transitory visual evoked potentials (TVEPs), brain state commands, visual evoked potentials (VEPs), evoked potentials such as the P300 evoked potential, sensory evoked potentials, motor evoked potentials, sensorimotor rhythms such as the mu rhythm or beta rhythm, event related desynchronization (ERDs), event-related synchronization (ERSs), slow cortical potentials (SCPs), etc., and other, as yet undiscovered, signature activity potentials underlying various cognitive or sensorimotor tasks. Neural activity can also be the frequency domain. Some examples among others include sensorimotor rhythms, Event Related Spectral Perturbations (ERSPs), specific signal frequency bands like Theta, Gamma or Mu rhythms etc.

As described herein, the neural recording headset 104 can record neural activity signals to gather information on user intentions through a recording stage that measures brain activity and translates the information into tractable electrical signals that can be converted into commands. In some embodiments, the neural recording headset 104 can be configured to record electrophysiological activity through electroencephalography (EEG) which has a high temporal resolution, low cost of set-up and maintenance, high portability, and is non-invasive to users. The neural recording headset 104 can include a set of electrodes having sensors that acquire electroencephalography signals from different brain areas. These sensors can measure electrical signals caused by the flow of electric currents during synaptic excitations of the dendrites in the neurons thereby relaying the effects of secondary currents. The neural signals can be recorded through the electrodes in the neural recording headset 104 appropriately arranged over desired brain areas when placed over the scalp of a user. Example neural recording headset may be available from commercial vendors like Biosemi, Wearable Sensing and G.Tec among others.

In some embodiments, the neural recording headset 104 can include electrodes, amplifiers, A/D converter, and a recording device. In some embodiments, the electrodes on the neural recording headset 104 can acquire the signal from the scalp and the amplifiers can magnify the analog signals to enlarge the amplitude of the neural signals. The neural recording headset 104 can be configured to have an appropriate number of signal acquisition channels to suit the number of electrodes. In some embodiments, the one or more electrodes arranged in the neural recording headset 104 can be connected to components like amplifiers, A/D convertors, and one or more recording devices to store signals from each electrode. In some embodiments, these components can be housed in the neural recording headset 104. In some embodiments, only the immediate signal amplification can be carried out in the neural recording headset 104 and the other processes like A/D conversion and recording can be carried out after transferring the signal to B-C Integrating Device 110. Signal transfer from the neural recording headset 104 can be configured through wired or wireless communication channels.

In some embodiments, the electrodes on the neural recording headset 104 can be arranged to be placed over the scalp based on the commonly followed International 10-20 system, standardized by the American Electroencephalographic Society. The 10-20 system uses two reference points on the head to define the electrode location. One of these reference points is the nasion, located at the top of the nose at the same level as the eyes. The other reference point is the inion, which is found in the bony lump at the base of the skull. The transverse and median planes divide the skull from these two points. In some other embodiments, the electrodes on the neural recording headset 104 can be arranged following any other suitable system. For example a 10-5 system or a custom electrode placement system. In some embodiments, the electrodes on the neural recording headset 104 can be placed symmetrically on the left and right sides of the head. In other embodiments, the electrodes can be placed asymmetrically on the left and right sides of the head. In other embodiments, the electrodes can be placed in specific parts of the head, for instance, around the top of the head, around the back of the head, around the ears, around the side of the head, or combinations thereof.

A neural signal is measured as the potential difference over time between an active electrode (also referred to as a signal electrode) and a reference electrode. In some embodiments, a third electrode, known as the ground electrode, can be used to measure the differential voltage between the active and the reference electrodes. In some embodiments, the neural recording headset 104 can include one or more active electrodes, one or more reference electrodes, and one ground electrode. In some embodiments, the neural recording headset 104 can include a few as seven active electrodes. In some embodiments, the neural recording headset can include up to 128 or 256 active electrodes. The electrodes can be made of silver chloride (AgCl) or any other suitable material. The electrodes can be configured so that the electrode-scalp contact impedance can be appropriately adjusted to record an accurate signal. In some embodiments, the neural recording headset 104 can have two or more active electrodes and fewer than 16 active electrodes, or in another embodiment, fewer than 12 active electrodes, or in another embodiment, fewer than 8 active electrodes.

Neural signals recorded non-invasively, across the scalp of a user, have to cross the scalp, skull, and many other layers which can make them weak and hard to acquire. Neural signals can also be affected by background noise generated either within the brain or externally over the scalp, which can impact the ability to extract meaningful information from the recorded signals. Embodiments of the system 100 including the neural recording headset 104 can incorporate several adaptations to improve neural signal acquisition. For example, a gel (i.e., a conductive gel) can be used to create a conductive path between the skin and each electrode to reduce the impedance. In some embodiments, the neural recording headset 104 can include "dry" electrodes that do not need the use of gels, which can be made with other materials such as titanium and stainless-steel. In some embodiments, the neural recording headset 104 can include dry active electrodes with pre-amplification circuits to accommodate the very high electrode/skin interfacial impedances. In some embodiments, the neural recording headset 104 can include dry passive electrodes that do not have any active circuits, but may be linked to a neural recording system configured with ultra-high input impedance. The amplitude of electrical bio-signals is typically on the order of microvolts. Consequently, the signal is very sensitive to electronic noise. In some embodiments, the BCI system 100 can be designed to reduce the effects of the noise with adaptations such as electromagnetic interference shielding or reduction for common mode signal, amongst others.

As described herein, the neural recording headset 104 can record neural activity signals to gather information on user intentions. The neural activity can be any form of a control signal indicating the user's intent. One example control signal can in the form of so called motor imagery signals. Motor imagery signals are neural activity signals associated with the user undergoing the mental process of motor imagery. The mental process of motor imagery involves a user rehearsing or simulating a particular action in their mind. For example, a user may imagine or simulate in their mind a swiping action of pointing a finger and turning their wrist. The motor imagery signals are brain signals recorded in the form of electrophysiological neural activity by a neural recording headset 104 for example, while the user imagines the action. The acquisition of motor imagery signals may or may not include actual motion by the user as described below.

Several studies of neural function have demonstrated that motor imagery is associated with the specific activation of the neural circuits involved in the early stage of motor control (i.e., motor programming). Studies of neural activity measured during actual motion and imagined motion indicate that motor imagery signals from imagined motion closely approximate the neural signals evoked during actual motion at least in a subset of brain regions. Some neural circuits include the supplementary motor area, the primary motor cortex, the inferior parietal cortex, the basal ganglia, and the cerebellum among other brain regions. Measurements of cardiac and respiratory activity during motor imagery and during actual motor performance revealed a covariation of heart rate and pulmonary ventilation with the degree of imagined effort. Thus motor imagery has been shown to activate motor pathways similar to planned performance of actual motion.

Some embodiments of the hybrid BCI system 100 can use motor imagery to implement the action control feature. For example, a hybrid BCI system 100 can be configured to receive neural activity signals recorded via the neural recording headset 104 appropriately arranged to collect neural activity data from brain regions known to contribute to motor imagery signals. The hybrid BCI system 100 can be used in either a trained fashion or in an untrained fashion to detect the motor imagery signals corresponding to specific motor actions imagined by the user. For example, the user may rehearse in a training session by performing motor imagery along with actual motions to teach the hybrid BCI system 100 to recognize one or more imagined gestures like swiping, pinching, zooming, and other simple or complex movements of the user's body. The hybrid BCI system can also use information gathered by peripheral sensors 108 like goniometers and torsiometers to help recognize the gesture in high detail during a training session or test session.

During operation (with or without training) motor imagery of specific gestures can be configured to implement specific actions. For example, motor imagery of the pinching gesture can be configured to implement a zoom out action in the UI. The neural activity data acquired from the neural recording headset can be analyzed for motor imagery signals and once detected and classified appropriately the BCI Device 110 can implement that particular action associated with the detected gesture on the desired portion of the UI. For example, if motor imagery signals corresponding to a pinching gesture is detected the UI can implement the pointing control feature to identify the portion of the UI where the action is desired and then implement the action control feature i.e. a zoom out effect on the desired portion.

Display and Presentation of the User Interface (UI)/User Experience (UX)

As described herein, the UI in the hybrid BCI system 100 functions as a link of communication between the user (e.g., the user's brain, eyes, etc.) and the BC Interfacing Device 110, and enables a user to focus and point at specific stimuli through the pointing control feature and select or deselect specific stimuli using the action control feature. The UI can be a sequence of visually stimulating two dimensional images, presented via a display. The UI can also be a rich mixture of stimuli in several modalities, together forming what can be called a UX that also acts as an interface. A strategically designed UX includes a process of presentation of stimuli to a user through any modality, some examples including visual stimuli, auditory stimuli, haptic stimuli, vestibular stimuli, or combinations thereof. In some embodiments, a UI that presents visual stimuli can be rendered on a display like the display 106 shown in FIG. 1. The stimuli of other modalities can be delivered though suitable peripheral actuators (not shown in FIG. 1) also being a part of the hybrid BCI system 100.

In some embodiments, the display 106 can be a separate, stand-alone, audio-visual display unit that can be connected and in data communication with the rest of the hybrid BCI system 100. That is, a stand-alone display (e.g., a liquid crystal display) equipped with an audio system (e.g., speakers, or headphones) can be in two-way communication with one or more of the other components of the hybrid BCI system 100, for example, the BC Interfacing Device 110, the video based eye-tracker 102, and the neural recording headset 104. In some embodiments, the display 106 can be integrated into the video based eye-tracker 102 to be part of the eye-glass area. The integrated video based eye-tracker 102 and display 106 can be configured to view virtual reality space in the form of a UI presented on the display 106. In some embodiments, the integrated video based eye-tracker 102 and display 106 can be configured such that the display 106 is on a semi-transparent eye-glass area, allowing the user to view augmented reality space. That is, the user can view the real-world through the semi-transparent eye-glass area that is also the integrated display 106 presenting the user with a UI that he/she can interact with.

Peripheral Devices Operating in Non-Visual Modalities

In some embodiments, the hybrid BCI system 100 can include several peripheral actuators 112 and sensors 108 shown as optional units in FIG. 1 (indicated by the dashed boxes). The one or more peripheral actuators 112 can be configured to deliver a rich multimodal UX and the one or more peripheral sensors 108 can be configured to capture multimodal input from the user and his/her environment, respectively. These peripheral actuators 112 and sensors 108 can be suitably mounted either individually or by being incorporated into other devices (like the video based eye-tracker 102). For example, the hybrid BCI system 100 can include earphones to relay auditory stimuli and microphones to capture sounds like the user's voice commands. The earphones (auditory sensors) and the microphones (auditory actuators) can be either stand-alone devices connected through wired or wireless channels to the hybrid system 100. Alternatively, they can be mounted and integrated with the video based eye-tracker 102 or the neural recording headset 104. Similarly, peripheral sensors like accelerometers, goniometers, torsiometers, can be included in the hybrid BCI system 100 to register body movements. For example, goniometers can be used register limb movements forming gestures, accelerometers can be used to register body movements. Peripheral sensors can also include a visual field camera configure to capture the real-world visual field of the user. The signals acquired by the visual field camera can be analyzed and used to generate and present the user with an augmented or mixed reality experience having real-world imagery superimposed by UIs with selectable options etc. Peripheral actuators that can be connected to a hybrid BCI system 100 can include haptic or kinesthetic devices that can apply and create forces like touch and vibration enriching the UX presented.

The Brain-Computer Interfacing Device

In some embodiments, the Brain—Computer Interfacing Device (or BCI Device) 110 can be configured to accomplish three main functions. First, the BCI Device 110 can be configured to generate a strategically designed UI or UX. For example, the strategically designed UX can be for a training session or for a testing session. In some embodiments, the UX can be designed as a virtual reality environment and/or as an augmented reality environment. In some embodiments, the UI can be tailored for specific needs such as, for example, specific user history, reaction times, user preferences, etc. The BCI Device 110 can account for all these requirements in the generation and updating of the UI/UX. Second, in addition to designing and generating the UI/UX, the BC Interfacing Device 110 can be configured to receive the pointing control signal (e.g., from the video based eye-tracker 102) and the action control signal (e.g., from the neural recording headset 104) and process the signals as an ensemble to determine the user's intent. Finally, the BCI Device 110 can be configured to implement the pointing control feature and the action control feature by (1) detecting meaningful features from the neural signals, and (2) implementing changes to the stimuli being pointed to per the user's intent. In some embodiments, the BCI Device 110 can also be connected to other peripheral devices, for example, peripheral sensors and actuators functioning in modalities other than the visual modality as mentioned above, that may be a part of the hybrid BCI system 100. Such peripheral sensors may include audio microphones, haptic sensors, accelerometers, goniometers etc., and peripheral actuators can include audio speakers, haptic stimulus providers, etc.

In some embodiments, the BCI Device 110 can include an Input/Output Unit 140 configured to receive and send signals to and from the BCI Device 110 to one or more external devices through wired or wireless communication channels. For example, the Input/Output Unit 140 can receive signals from and send signals to the video based eye-tracker 102, the neural recording headset 104, and the optional audio visual display 106 through one or more data communication ports. The BCI Device 110 can also be configured to be able to connect to remote servers (not shown in FIG. 1) and access databases or other suitable information contained in remote servers. The BCI Device 110 can include a Communicator 180 configured to handle suitable channels of communication adapting to the type of data to be transferred. The Communicator 180 can be connected to the I/O Unit 140 among other parts of the BCI Device 110 and control the functions of the Input/Output Unit 140. The transfer of signals can also be carried out through a wired connection like wired Ethernet, Serial, FireWire, or USB connection, or wirelessly through any suitable communication channel like Bluetooth, Nearfield communication, etc.

In some embodiments, the functions of the Input/Output Unit 140 in the BCI Device 110 can include several procedures like signal acquisition, signal preprocessing and/or signal enhancement, etc. The acquired and/or pre-processed signal can be channeled to a processor 120 within the BC Interfacing Device 110. In some embodiments, the processor 120 and its sub-components (not shown) can be configured to handle the incoming data, send and retrieve data to and from a memory 160. The processor 120 can also be connected to the communicator 180 to access and avail information from remote servers (not shown in FIG. 1).

The processor 120 in the BCI Device 110 can be configured to carry out the functions of building and maintaining a UI which can be rendered on the display 106 or on a display integrated with the video based eye-tracker 102. In some embodiments, the processor 120 and its sub-components can be configured to carry out the functions needed to enable user-specific interpretation of brain signals, and packaging output signals to the Input/Output Unit 140 to be relayed to external devices. Other functions of the processor 120 and its sub-components can include several procedures like feature extraction, classification, and manipulation of the control interface.

Pointing and Selecting an Option—Working of a Hybrid BCI System

Figure 2:
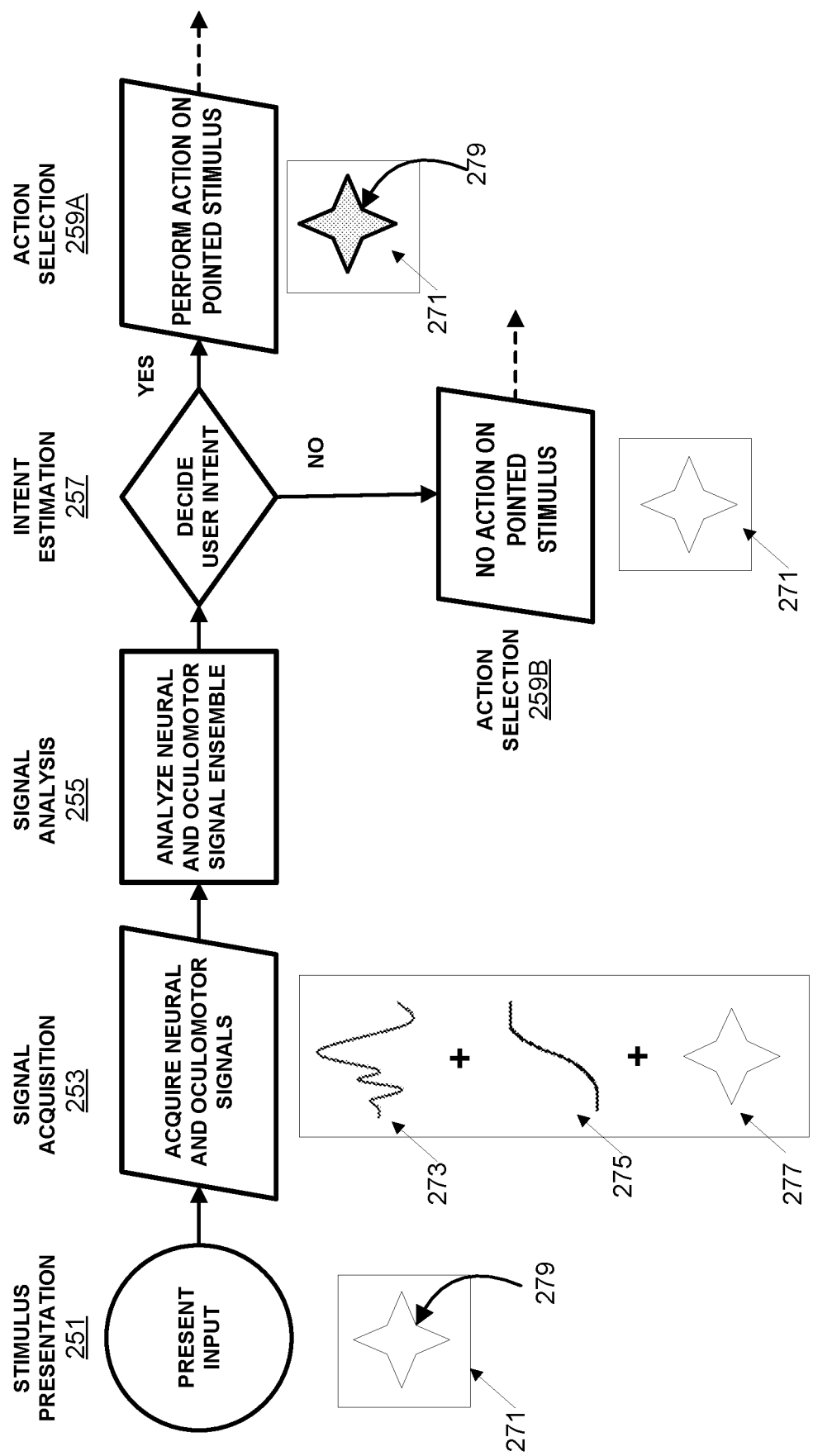
FIG. 2 shows an illustration of the sequence of steps involved in an example implementation of a pointing control feature and an action control feature to select/deselect a stimulus icon, using an embodiment of the hybrid BCI Device.

FIG. 2 shows, the working of a hybrid BCI system for one example instantiation of a user focusing on and controlling the selection of an example input symbol. The illustrative example sequence of operational events in FIG. 2 includes capturing the oculomotor signals and the neural activity of one or more users during the presentation of a UI or UX, interpreting these signals to deduce the user's intent, and effecting change in by controlling one or more machines via the UI. This example instance of working of the hybrid BCI system begins at the presentation of an input stimulus (e.g. a symbol) at step 251 through a UI 271. Upon presentation of the stimulus, and following eye-movement and neural responses from the user, in step 253 the hybrid BCI system acquires one or more oculomotor signals 275 (e.g., indicating eye movements implementing the pointing control feature from a video based eye-tracker). In step 253, the hybrid BCI system can also receive one or more neural activity signals 273 (e.g., implementing the action control feature indicating the cognitive intent of the user from a neural recording headset). This signal acquisition step 253 can include receiving signals from other peripheral sensors and actuators as well as receiving information about stimulus presentation indicated by the stimulus information 277 in FIG. 2.

Step 255 includes ensemble analysis of the acquired oculomotor signals 275 and neural signals 273 which can be carried out in an integrated approach as disclosed below. The ensemble analysis of signals from the video based eye-tracker, the neural recording headset and other peripheral devices is performed in the context of stimulus information 277 (for example, the spatiotemporal properties of the presented stimulus). Upon analysis, in the decision step 257, the hybrid BCI system can estimate the user's intent using information from several sources, for example, the acquired signals, information about the stimulus being presented through the UI 271, prior information about the user, context of usage of the UI 271 and the hybrid BCI system. The decision to act upon the user's intent may be followed by any suitable action. For example, a prediction to select or deselect the presented stimulus. The estimation of user's intent can be performed though one or more estimation methods using one or more Machine Learning tools. The decision step 257 can use one or more criteria or threshold to determine the user's intent based any suitable threshold crossing algorithm. For example, if the results of the estimation do cross the threshold criterion, the hybrid BCI system can proceed to step 259A which involves selecting the stimulus or symbol presented in the UI 271 which may lead a suitable change to a connected machine. On the other hand, for example, if at step 257 the estimated value does not cross the threshold criterion the hybrid BCI system can proceed to step 259B which involves no selection of the stimulus or symbol in the interface 271.

User Interaction with the Hybrid BCI System

FIGS. 3A-3E illustrates an example user interaction with the hybrid BCI system 100, according to an embodiment. In this example, the hybrid BCI system 100 is being used to spell words in a two-step process, and the display 106 presents several a UI 371 sub-groupings of characters (e.g., letters, numbers and symbols commonly found on a keyboard) in FIG. 3A. The user wears a video based eye-tracker 102 and a neural recording headset 104, shown in FIG. 3C. When the user focuses their gaze on a sub-group containing the desired letter (e.g., the sub-group indicated by the highlighted circle in FIG. 3A), the UI 371 presented in the display 106 changes to that shown in FIG. 3B where focused sub-group is magnified. The user can then perform the action of selecting a letter by focusing their gaze on the specific desired letter in that sub-group. The action control feature is then implemented by using the neural activity recorded to perform the selection of a letter to be used in forming a word or a sentence.

Figures 3A, 3B:
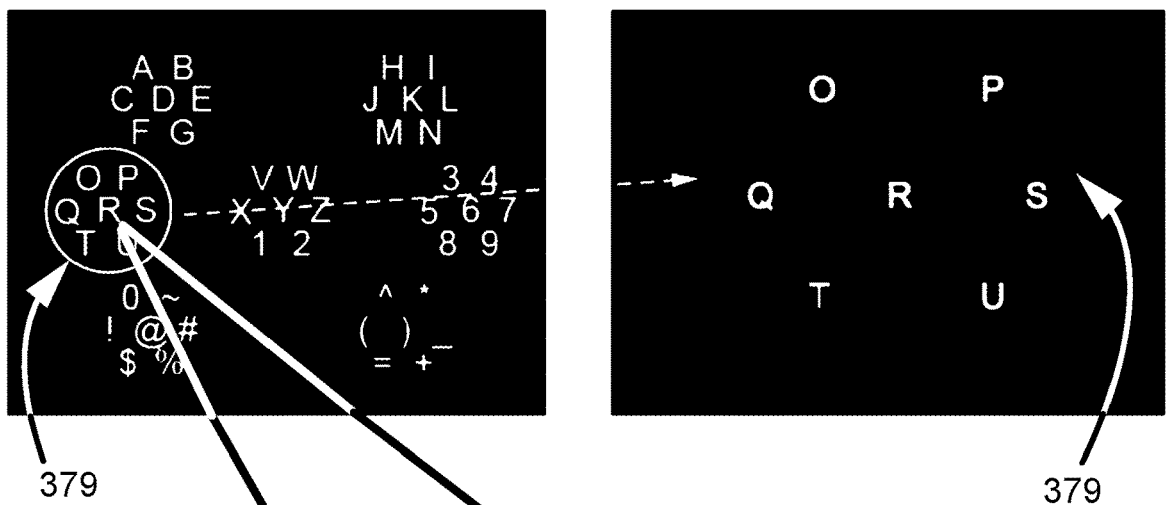
FIGS. 3A and 3B show the UI before and after user interaction.
Figure 3C:
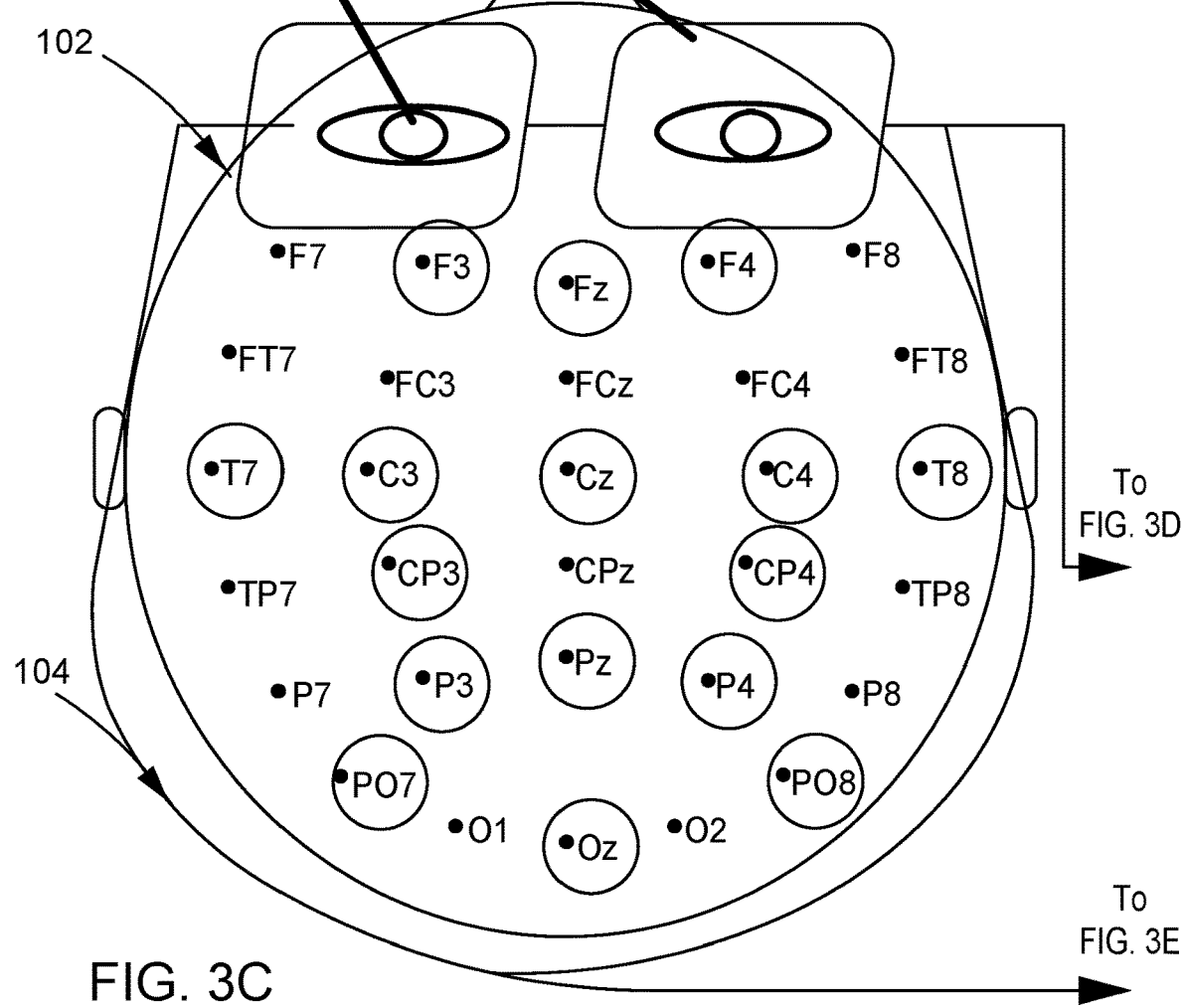
FIG. 3C shows the user mounted with a video based eye-tracker and a neural recording headset, according to an embodiment.
Figure 3D:
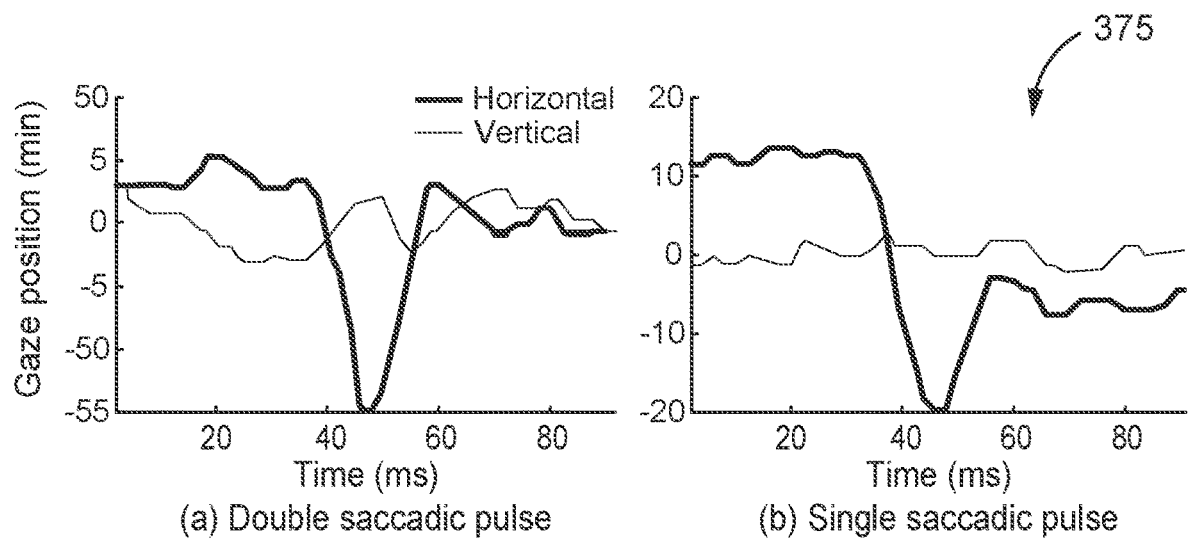
FIGS. 3D and 3E show example signals acquired by the video based eye-tracker and the neural recording headset shown in FIG. 3C.
Figure 3E:
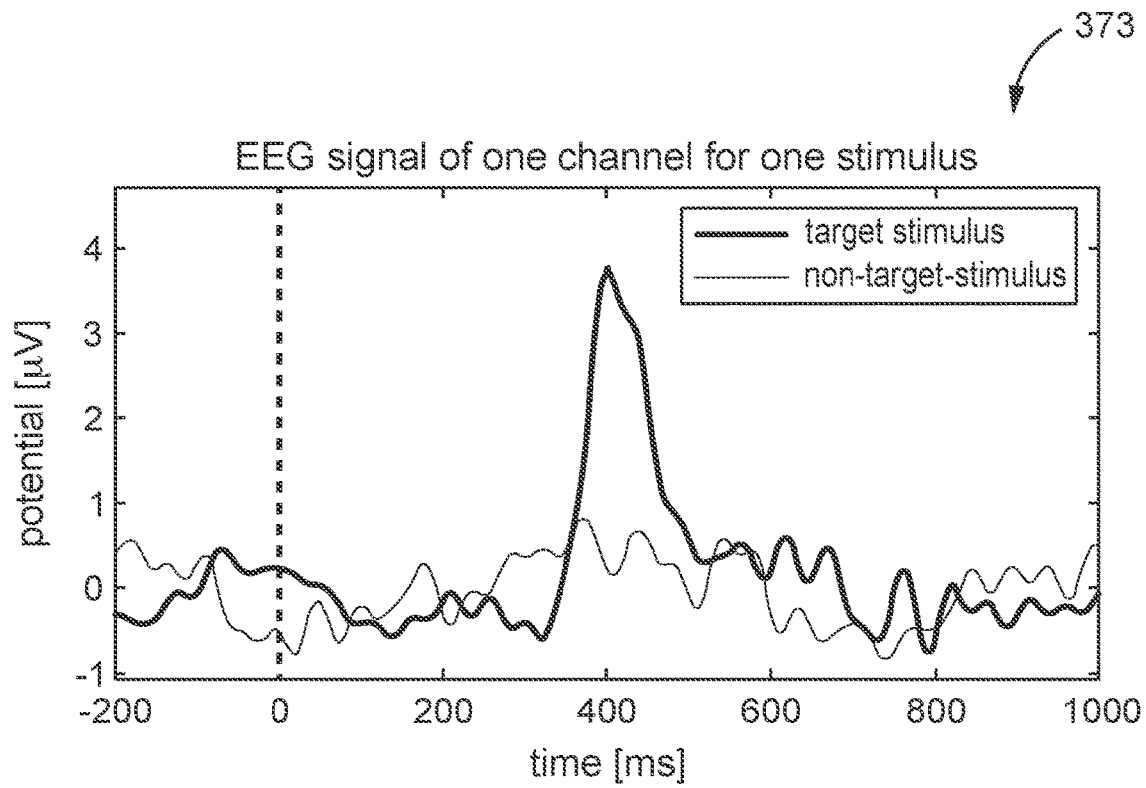

The pointing control feature described above with reference to FIGS. 3A and 3B, is implemented with the data acquired by the video based eye-tracker 102 shown in FIG. 3C. The video based eye-tracker 102 can be configured to detect where the user is focusing their gaze, and then output a signal as shown, for example, in FIG. 3D. Additionally or alternatively, the video based eye-tracker 102 can be configured to detect where the user is not focusing their gaze. The action control feature (i.e., activation of a stimulus or symbol) is implemented with the data recorded by the neural recording headset 104 shown in FIG. 3C. The neural recording headset 104 is configured to record neural signals from the user's brain, and then output a signal as shown, for example, in FIG. 3E. A processor (not shown) can then extract meaningful features from the eye-tracking signal (FIG. 3D) and the neural signal (FIG. 3E) as an ensemble, and analyze them either in an unsupervised and/or semi supervised manner or by classifying the signals based on prior models built through rigorous training with each specific user. The analyzed data can then be used to make predictions of user behavior such as the point of focus of the user and/or the selection or activation of a symbol upon which focus is predicted.

Operating the Hybrid BCI System

Figure 4:
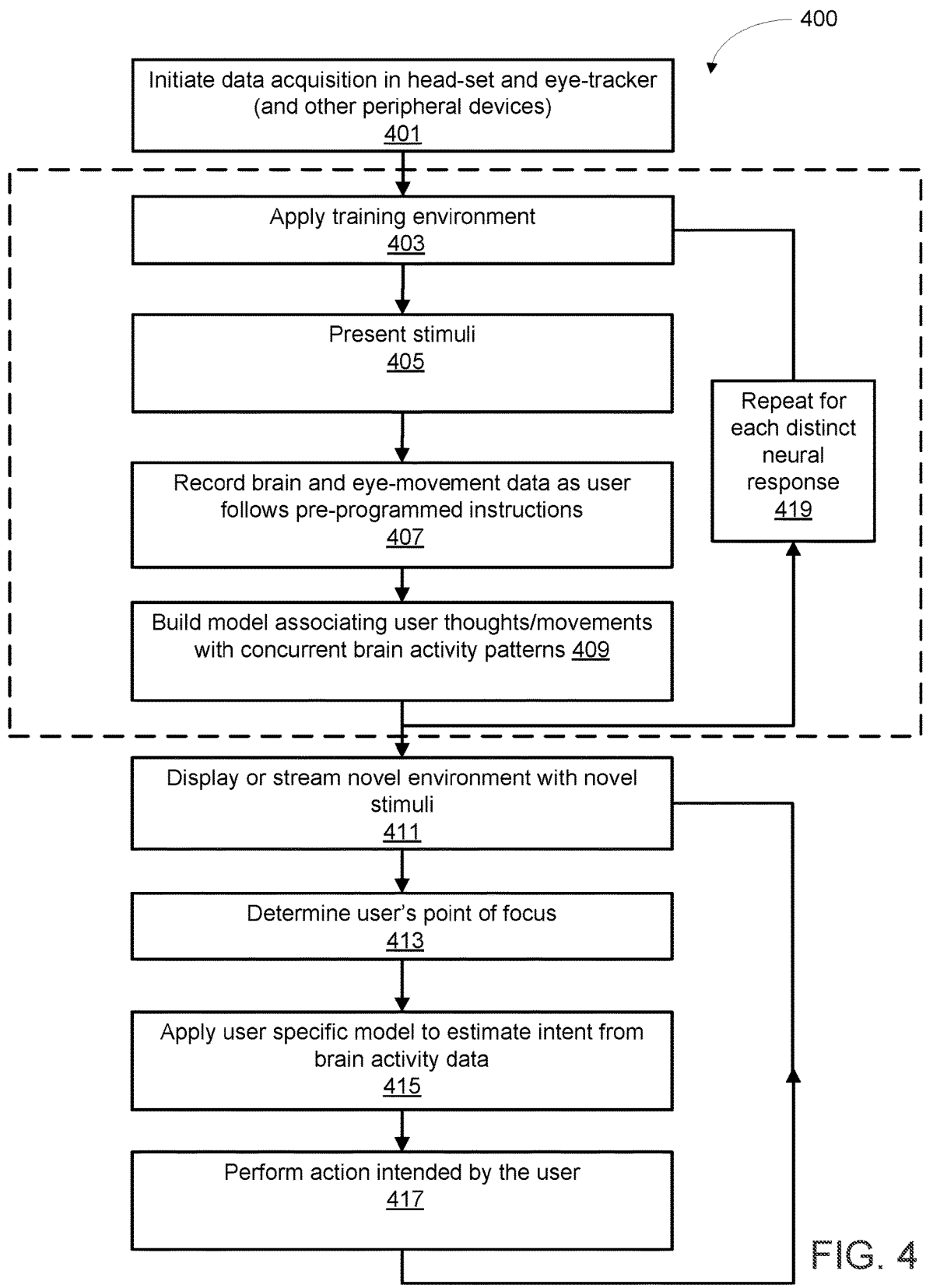
FIG. 4 shows an example process of operation of a hybrid Brain Computer Interfacing Device, according to an embodiment.

While the process sequence illustrated in FIG. 2 and the example pointing control and action control implementation shown in FIGS. 3A-3E can be instantiated for an individual stimulus, a similar process with a similar sequence of steps can be followed during the presentation of virtual or augmented, multimodal, environments via a UI or UX. As shown in FIG. 4 the process 400 can include a sequence of sub-steps that form a training session (indicated as optional by a box with dashed lines) or can be used for presentation of novel stimuli without any training data.

The example process 400 shown in FIG. 4 includes an initial step 401 of initiating data acquisition and pre-processing for a particular user associated with a neural recording headset and an eye-tracker (and other peripheral sensors and/or actuators) at a time-point. For example, this initiation and signal acquisition can be carried out by components that are a part of the processor in the BCI Device, in the hybrid BCI system.

The process 400 can include a sub-set of steps (optionally used for training sessions, indicated within the dashed box in FIG. 4) for the purpose of generation of generation and training of a statistical model. The sub-set of steps for the training session can include a step 403 of applying a training environment generated to present a user with a series of inputs to record and store the user's oculomotor and neural response for later use. The presentation of the training environment can include a set of pre-determined, controlled stimuli presented in step 405 and the ensuing eye movement and brain activity can be recorded in step 407. In step 409 the acquired responses can be paired with the known stimulus causing the responses and fed into a model built through the pairing and association. The presentation of varied, but controlled stimuli and collection of corresponding oculomotor and neural activity data can be repeated for each set of oculomotor-neural responses as shown by step 419 for a sequence of stimuli in one or more repeated presentations. The model generated from the association of know stimuli and recorded oculomotor-neural responses can be updated with each set of new stimulus-response pairs in the training set.

Either following a training session or without a training session a user can be presented with stimuli through a UI or UX following initiation of data acquisition in step 401. This is shown in step 411 of the process 400. The step 411 can include the presentation of a new environment containing one or more novel stimuli or accustomed stimuli which may be associated with one or more of the preprogrammed stimuli presented during training. The hybrid BCI system can either generate a new statistical model or use a pre-built statistical model generated during training. Using the statistical model for analyzing the oculomotor and neural activity responses of the user the hybrid BCI system can determine the user's point of focus (through the pointing control feature) in step 413 and estimate the user's intent in step 417. Following which in step 417 the hybrid BCI system can implement the action control feature by performing the action intended by the user (as determined by the analysis of the neural activity data). For example, the step 417 can include selection of a letter in a speller, or selection of a character in a game, or the selection of ON functionality associated with a TV system that can be operated in an augmented reality system.

An Example Hybrid BCI System

Figure 5:
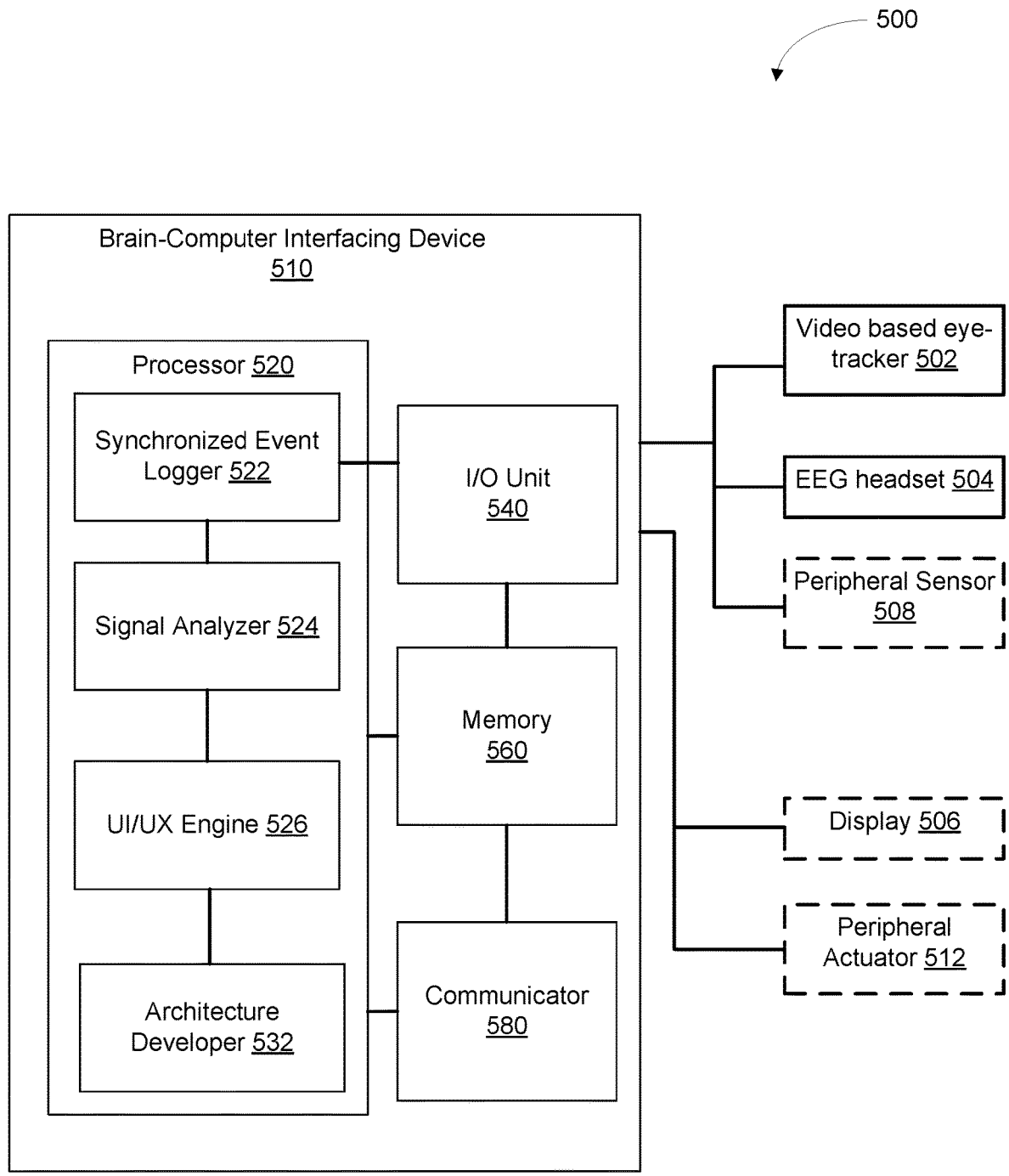
FIG. 5 is a schematic illustration of a hybrid Brain Computer Interfacing Device, according to an embodiment.

FIG. 5 shows a hybrid BCI system 500 according to an embodiment. In some embodiments, the BCI system 500 can be similar in structure and/or function to the corresponding portions of the hybrid BCI system 100 described above with reference to FIG. 1. For example, the BCI system 500 includes a video based eye-tracker 506, an neural recording headset 504, an optional display 506, and a Brain-Computer Interfacing Device 510 that can be the same or similar to the video based eye-tracker 106, the neural recording headset 104, the optional display 106, and the Brain-Computer Interfacing Device 110 of the hybrid BCI system 100. Accordingly, such similar portions and/or aspects are not described in further detail herein.

In some embodiments, the Brain Computer Interfacing Device 510 can include an I/O Unit 540, a Memory 560 and a Communicator 580, in addition to a Processor 520. These components can be connected to each other through wired or wireless connections. The processor 520 of the Brain-Computer Interfacing Device 510 can in turn include a Synchronized Event Logger 522, a Signal Analyzer 524, a UI/UX Engine 526 and an Architecture Developer 532, all units interconnected to each other and configured to access and transfer information between each other.

The Synchronized Event Logger 522 can receive the acquired eye-tracking oculomotor signals, the neural activity signals, and other incoming signals from various peripheral devices, via an I/O unit 540. The Synchronized Event Logger 522 can timestamp the signal data to be synchronous with each other and perform any pre-processing required for further analysis. In some embodiments, the Synchronized Event Logger 522 can be configured to perform high-speed eye movement detection and classification as described below.

In some embodiments, the Brain-Computer Interfacing Device 510 can include a Signal Analyzer 524 that can be configured to implement ensemble estimation of attention using disparate physiological signals as described in examples of the integrated approach below. The Brain-Computer Interfacing Device 510 can also be configured to use parallelization and asynchronous processing of separable components in the pipeline to ensure performance on consumer-level personal computers.

In some embodiments, the processor 520 can include a UI/UX Engine 526 that is configured to generate and present a training environment (in the case where a training session is required rendered through the UI. The training environment can be configured to present a user with a set of predetermined controlled stimuli and record the ensuing eye movement and/or brain activity. This set of controlled stimuli and the evoked eye and brain activity corresponding to each of the controlled stimuli can then be stored in a memory 560 and used by the Signal Analyzer 524 as training data to build statistical models that are tailor made for individual users. The Signal Analyzer 524 can use one or more statistical tools like dimensionality reduction methods, feature extraction methods, machine learning tools to build classifiers etc. The Signal Analyzer 524 can also access and use information from remote sources (e.g. remote servers, data bases, etc.) through a Communicator 580 that is part of the BCI Device 510. The models can be built, tested and cross-validated using the training data provided. The tested models can then be used by the Signal Analyzer 524 over new oculomotor—and neural activity data acquired from that particular user to achieve a high accuracy and speed of interaction with the UI.

In some embodiments, the Signal Analyzer 524 in combination with the UI/UX Engine 526 can classify the data based on results from the statistical testing and generate a prediction for user behavior using tools like maximum likelihood estimation, maximum a posteriori estimation, etc. In some embodiments, the processor 520 can also include a Architecture Developer 532 that receives the oculomotor and neural activity data as well as data from the other sub-components of the processor 520 (e.g., the Signal Analyzer 524, the UI/UX Engine 526, and from external remote sources through the Communicator 580). The Architecture Developer 532 may not be intended for real-time use, but for robust statistical analyses off-line towards prototyping potential BCI algorithmic detection architectures.

An Integrated Approach to Signal Analysis

As described herein, the hybrid BCI systems 100, 500 can process oculomotor signals in conjunction with neural activity signals, in addition to other appropriate signals, in an integrated manner, to implement the pointing control and action control features of the BCI system with high speed and accuracy. In some embodiments, the pointing control feature can be implemented in a hybrid fashion using several sources of information. That is, the BC Interfacing Device 110 (or 510) can be configured to process the integrated signals as an ensemble. For example, in some embodiments, the video based eye-tracker 102 can be used to detect any suitable form of eye movement information, for example, saccadic, foveation and/or pupil dilation information, as well as foveation information, through oculomotor data conveying movement of the eye muscles. Information about saccadic eye position can also be indirectly obtained from neural activity, for example, ERPs that are evoked by visual responses, acquired from the neural recording headset 104. For example, the hybrid BCI systems 100,500 can be configured to correlate the occurrence of ERPs with the presentation of a particular stimulus in time and space to form a causal relationship. Indirect information about gaze position can also be obtained from knowledge of the manner in which the stimulus was generated by UI/UX Engine and presented to the user. Thus, oculomotor data from the video based eye-tracker 102 can be combined with data from visually evoked neural activity from the neural recording headset 104, and the strategic presentation of stimuli in the UI delivered through the display 506 before being analyzed by a Signal Analyzer 524. Additionally, in some embodiments, the Signal Analyzer 524 can also include data from a theoretical model of gaze kinematics or a biological model of the user's eyes to inform the estimate of eye-position to implement the pointing control feature. The models can include binocular vision parameters to estimate depth of focus to enable pointing control in three-dimensional space.

An integrated hybrid approach to tracking pointing control allows a user to rapidly select a target by voluntary movement of their eye-gaze, with the various signals from the video based eye-tracker 102, the visually evoked neural activity from neural recording headset 104, information about the properties of the stimulus presented, and data from the theoretical models complementing each other in the information provided to locate gaze. The user visually fixes attention on a target and the BC Interfacing Device 110 can identify the target through features analysis of the combined package of signals informative about gaze. Notably, in the hybrid BCI system 100, the signals in the combined package are analyzed as an ensemble, with appropriate weighting for each signal source, by the BC Interfacing Device 110.

One of the advantages of using the integrated approach to implementing the pointing control feature is that the eye position can be estimated very rapidly in real-time. The integrated approach also allows most robust estimation as the video based eye-tracker 102 may not be susceptible to the same noise sources as neural activity recorded through the neural recording headset 104 and vice versa. Thus, one channel can compensate for the weaknesses of the other. Furthermore, the approach of processing both data sets as an ensemble allows the appropriate weighting of the individual signals according to other parameters like user history and specific details of the interface navigated, etc. In addition the Signal Analyzer 524 can be configured to implement a suitable analytical pipeline that uses: (1) suitable processing of the signal through one or more filtration systems (e.g. a dual kalman filter, or any other lagless filter), (2) a Bayesian linear discriminant system, (3) spatial filtering over the weighted signal package, (4) a bagging ensemble classifier algorithm, and (5) a higher-order oracle algorithm that incorporates information from the classification algorithm with program routines during the experimental task, to improve selection accuracy.

The hybrid BCI systems 100, 500 also use an integrated approach to implementing the action control feature. In some embodiments, for example, the Signal Analyzer 524 can combine neural activity data from the neural recording headset 504 with a statistical model built from training data, or theoretical models of human cognition and oculomotor data from the video based eye-tracker 502 (conveying brain states like attention from parameters like pupil dilation etc.), and multimodal sensory data from various peripheral sensors. The Signal Analyzer 524 can perform ensemble distance estimation and classification using a suitable suite of machine learning tools and statistical classifiers to reduce the estimation to a simple value or threshold crossing signal. This reduced signal can be then used to implement the action control feature upon the symbol or stimulus of desire. To improve user experience, the hybrid BCI systems 100, 500 can be tuned to optimize for speed, such that the implementation of the action control occurs within 5 seconds, or within 4 seconds, or within 3 seconds, or within 2 seconds, or within 1 second, or within 0.9 seconds, or within 0.8 seconds, or within 0.7 seconds, or within 0.6 seconds, or within 0.5 seconds. To improve user experience, the hybrid BCI systems 100, 500 can be tuned to reduce or minimize a value of speed*accuracy %, such that the implementation of the action control speed (in seconds) times the average accuracy of the system (in %) is less than 5 (e.g., 10 s*50% accuracy), or y less than 4, or less than 3, less than 2, or less than 1.125 (e.g., 1.5 s*75% accuracy), or less than 1, or less than 0.9 (e.g., 1 s*90% accuracy), or less than 0.8, or less than 0.7, or less than 0.6, or less than 0.5 (e.g. 0.6 s*83.33% accuracy).

Adaptations in the UI/UX

As described herein, the operation of the hybrid BCI systems 100, 500 includes a UI or UX that is central to the functioning of the hybrid BCI system. The UI or the UX acts as a communicating link between the user (e.g., the user's brain, eyes, etc.) and the BC Interfacing Device 110, and enables a user to focus and point at specific stimuli through the pointing control feature and select or deselect specific stimuli using the action control feature. In a simple example, the UI can be a sequence of visually stimulating two dimensional images, presented via a display. Examples of UIs presenting visual stimuli as displayed on a display (like the display 106) are shown in FIG. 2 (UI 271) and FIG. 3 (UI 371).

The UI can also be a rich mixture of stimuli in several modalities, together forming what can be called a UX that also acts as an interface. A strategically designed UX includes a process of presentation of stimuli to a user through any modality, some examples including visual stimuli, auditory stimuli, haptic stimuli or vestibular stimuli. The UI or UX can be designed and generated by the UI/UX Engine 526 of the system hybrid BCI systems 500. The UI/UX Engine 526 can operate in combination with the Signal Analyzer 524 updating the UX presented with data output from the Signal Analyzer 524. For example, the UX can be updated according to the estimated user intent thereby implementing the action control feature.

The UI/UX Engine 526 can also operate in combination with the Architecture Developer 532 to generate and maintain an appropriate UI or experience according to the requirements of the users and the context of usage of the hybrid BCI system. The UI/UX Engine 526 can be configured to update the UI in real-time based on feedback from the user or the user's environment through either the oculomotor signals recorded from the video based eye-tracker 102 or the neural recording headset 104, or one more other peripheral devices which may be sensors and actuators including an on-scene camera that may capture the immediate environment. The UI/UX Engine 524 can also be configured to update the processor 520 in the BCI Device 510 in accordance with the user feedback and the updated UI such that the BCI Device 510 can support the background processing required to maintain the UI and analyze the incoming signals. For example, the UI/UX Engine 524 can supply stimulus properties to the Signal Analyzer 524 for the ensemble estimation and implementation of the pointing control and action control features. In some embodiments, the UI/UX Engine 526 can also switch modes of processing in the Signal Analyzer 524, for example, if the UI switches from a visual modality to an audio-visual modality of interaction. Some example implementations of a UI are disclosed below.

Dynamic Stimuli

In some embodiments, the UI can be configured to consist of not only static visual images but a running sequence of visual images forming a video. The video can be a synthetically generated sequence of images programed within the BCI Device 510 by the UI/UX Engine 526 or obtained from a remote source though the Communicator 580 and updated to suit the UI desired. The synthetically generated or obtained video can be relayed to the user through the display (106, 506). The video can also include a sequence of real-time events occurring in the real world environment of the user, relayed to the user and copied to the BCI device 510 through any suitable pair of glasses that include a visual-field camera capturing the user's field of view. In some embodiments, the eye-glasses and the visual field camera can be incorporated on the video based eye-tracker 102.

Figure 6:
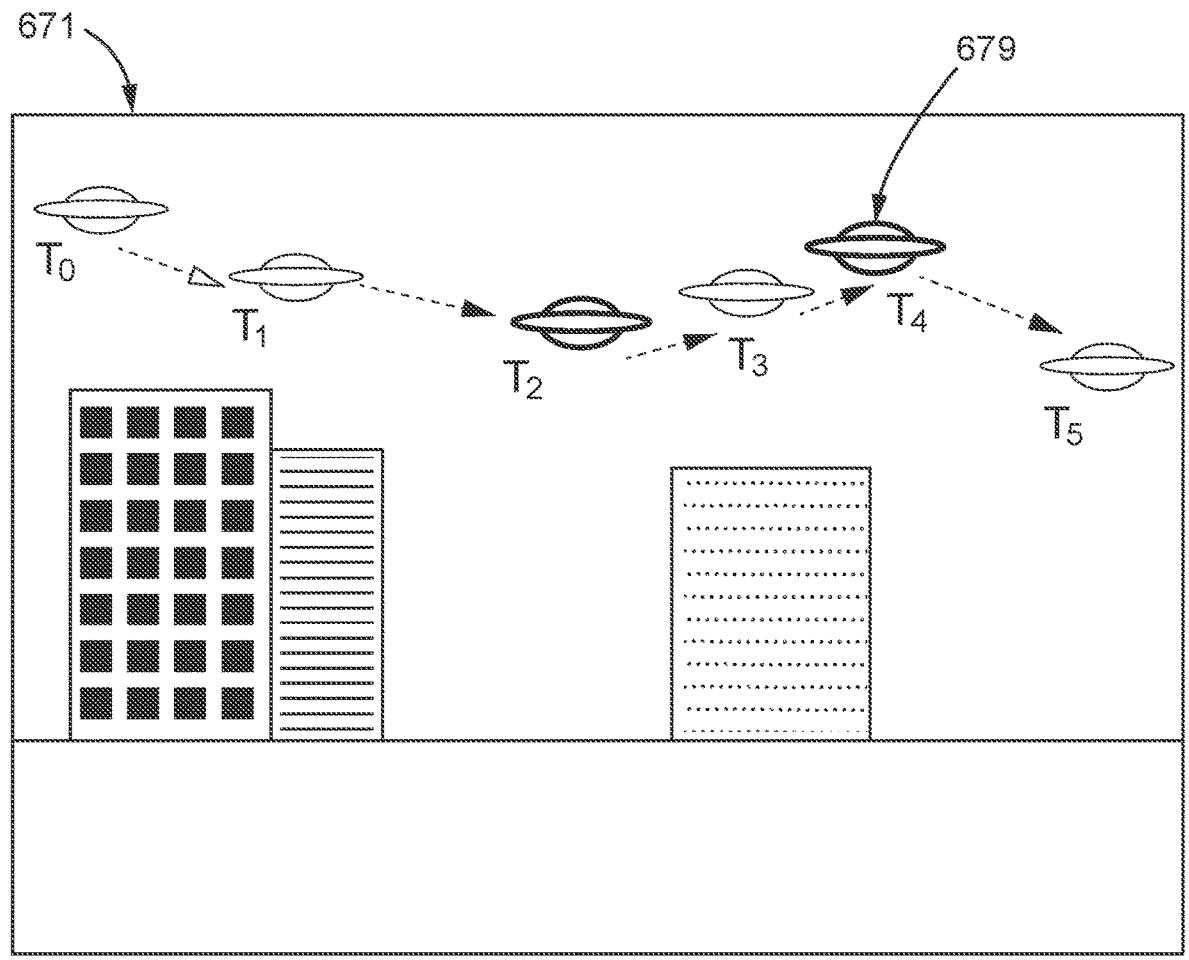
FIG. 6 shows an example UI of a hybrid BCI system illustrating the identification and tracking of a dynamic stimulus, according to an embodiment.

In some embodiments, visual stimuli in the form of videos can be treated as dynamic stimuli with moving targets. FIG. 6 shows an illustration of an example dynamic object moving through space. The BCI Device 510 can be configured to perform suitable image processing routines to identify moving targets and track their dynamic movements through time and space by analyzing the video (generated, obtained, or captured through the visual field camera). During image processing, the BCI Device 510 can also be configured to perform searches and access information from databases or repositories of image or video data held in remote servers by establishing communication channels through the Communicator 580. The Signal Analyzer 524 and the UI/UX Engine 526 can operate in combination to carryout analytical routines like image segmentation, contour detection, movement detection, etc. The BCI Device 510 can use any suitable suite of statistical methods to identify and track the moving dynamic stimuli. It can also incorporate prior knowledge of the user's behavior or the context of the UI or UX stored in the Memory 560 to help with identification and tracking of dynamic stimuli.

Once identified, the dynamic stimulus can be assigned a tag, as shown in the example illustration of a UI 671 in FIG. 6. The tags $T_0$, $T_1$ ... T5 can be points in time each designating a particular event associated with the dynamic stimulus. For example, $T_0$ can indicate the time point in which the dynamic stimulus appears and is detected first. $T_5$ can indicate the end of tracking of the stimulus before it disappears. Each tag and the associated information can be stored as part of the stimulus information (e.g., stimulus information 677) which can be used in several other analyses including ensemble estimation of eye position to implement the pointing control feature or ensemble estimation of user intent to implement the action control feature. For example, the object can be identified and tagged such that when the user's point of gaze is detected to pass over the tracked object in space and time, the tracked dynamic object can flash (as indicated by the tag $T_4$ in the example in FIG. 6). The user can then use their thoughts to manipulate the object. That is, the simultaneously recorded neural activity data having undergone ensemble processing can be used to determine the user's intent with regard to the dynamic object. If a signature neural activity (e.g., an ERP or a motor imagery signal) is detected this may indicate the user's desire to trigger an action associated with that dynamic object. The action can be based on the properties of the dynamic stimulus as well as the neural activity being recorded and analyzed. For example, the action can be a simple selection to view a menu associated with the object or the action can a complicated maneuver of the object by using motor imagery signals as disclosed in examples below. Any such selection or triggered action resulting from the selection of the dynamic object at any instance can also be stored as part of the stimulus information 677 for future use.

Three-Dimensional UX

The hybrid BCI systems 100, 500 and other embodiments described herein can be configured to support a two dimensional or three-dimensional UI or UX in spatial dimensions. As described herein, the UI or UX can be a completely virtual environment generated by the UI/UX Engine 526. Or the UI/UX can be the real-world environment of the user relayed through eye-glasses and superimposed with a UI that makes it an experience of augmented reality for the user.

In some example implementations, the UI can be a simple system offering a set of control tools in the form of menus and icons and implementing the pointing control feature and the action control feature in two dimensional space or in three-dimensional space (i.e., utilizing depth of vision). In some implementations, the UI can also be a rich three-dimensional experience with multimodal presentation a virtual (or augmented) space that can be navigated by the user providing an experience similar to real world navigation. The UI can also include combinations of these and various other types of stimulus presentations arranged appropriately to suit the contextual requirement of the user.

The hybrid BCI systems 100, 500 can use properties of how the human visual system processes depth in three dimensions to both generate the UX and to analyze the oculomotor and neural signal during ensemble processing. For example, the human visual system uses several cue to determine whether objects in the visual field are from different depth of vision. One example property is partial occlusion. When one object is occluded by another there is reasonable expectation of the occluded object to position behind the occluding object. This can be used to generate three-dimensional space in the virtual environment. This property can also be used when implementing the pointing control feature to accurately determine that the user's point of focus is on the object in full view and not the object being occluded from vision.

Another example property is the relative size and shape of know objects as they change with depth of vision. For example, if two objects have a known size and shape, and one appears smaller than the other, it can be reasonably estimated that the smaller object is farther in spatial distance from the observer than the larger object. This property also can be used to render objects in varying sizes and in varying perspective views by the UI/UX Engine 526 to generate a real three-dimensional virtual space. This property can also be used to accurately determine the point of focus of the user.

Additionally, the human visual system also uses information from binocular vision relaying the relative movements of one eye with respect to the other and the depth of focus of each eye to determine the position of objects in the real world, otherwise termed stereoscopic eye tracking. The hybrid BCI systems 100, 500 can perform stereoscopic eye tracking and use eye movement signals from both eyes collected by the video based eye-tracker 102, 502 and use the signals to generate a binocular estimation of depth of focus. This binocular estimation can be combined with other sources of depth information to accurately estimate the depth of object in view of the user in real, virtual or augmented space.

Navigation Control

In some embodiments, the hybrid BCI systems 100, 500 can include the presentation of a UX either in two or three-dimensional space that involves navigation. For example, the UI can be configured to play a navigational game like Pacman or Quake. In other instances, the UI can be configured to navigate a user's wheelchair in the real world. The UI/UX Engine 526 can use context based information provided by the user, the BCI Device 110 (510), or from the user's environment (relayed through a visual field camera) and generate/update the UI or UX presented with appropriate controls to mediate navigation. An example illustration of a navigation control interface according to one embodiment is illustrated in FIG. 7.

Figure 7:
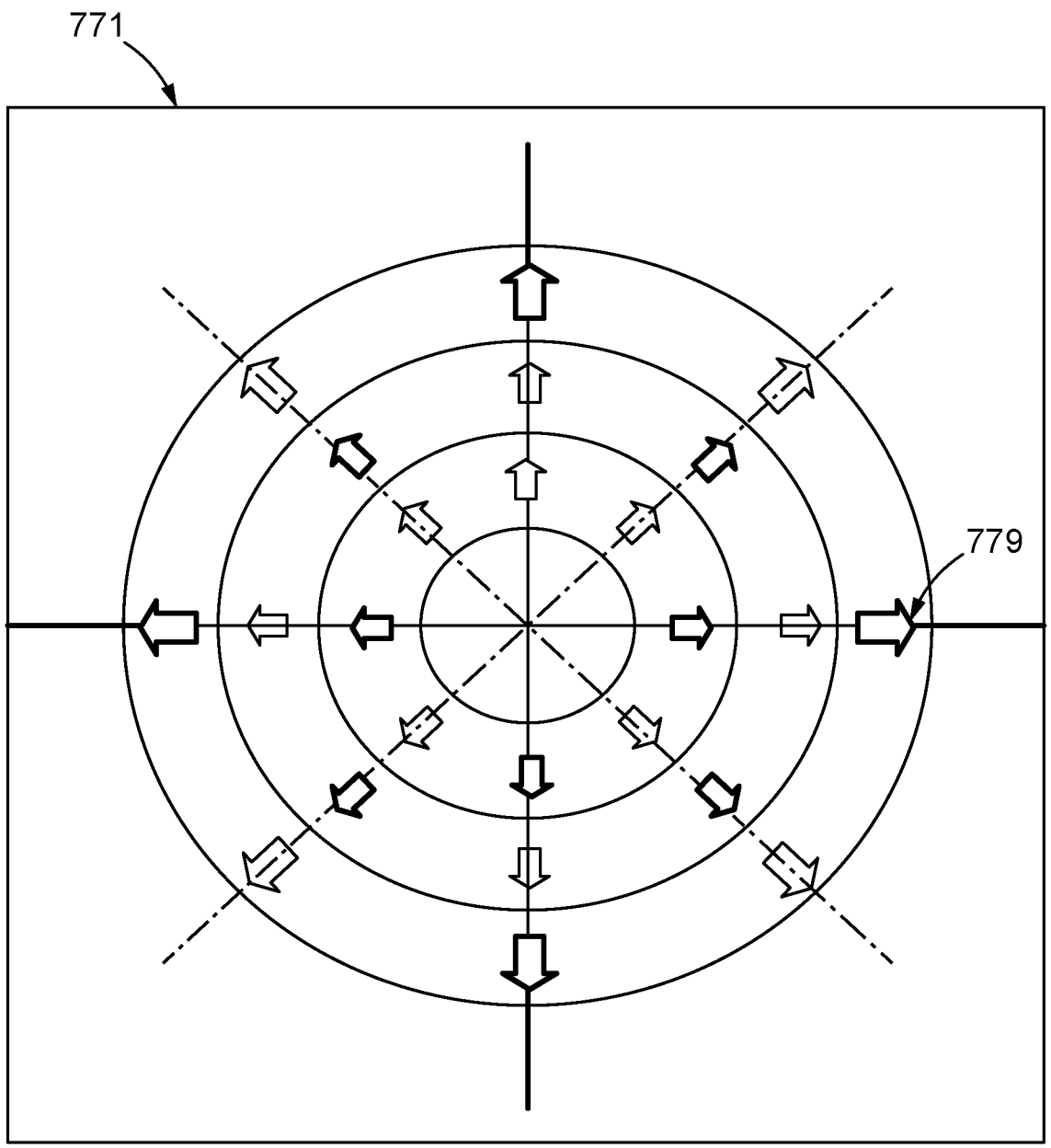
FIG. 7 shows an illustration of an example navigation control in a UI of a hybrid BCI system, according to an embodiment.

In some embodiments, the hybrid BCI systems 100, 500 can present a user with navigation control interface like that shown in FIG. 7, based on the context of the user's environment or explicit instruction from the user. The navigation control interface can provide control over movement velocity and movement direction. For example the navigation control interface can include a transparent overlay of concentric circles with each ring representing a velocity zone. Each ring can also include symmetric outlay of symbols, for example arrows, that can be activated or inactivated. The symbols or arrows can be configured to control movement by starting and stopping selection of the associated velocity band. The angle and position of each arrow can indicate the direction of movement.

In some embodiments, a navigation interface similar to the one disclosed above and shown in FIG. 7, can be operated by implementing the pointing control feature and the action control feature in combination. For example, the pointing control feature can be used to determine the user desired arrow indicating the direction of movement. The action control feature can be implemented to select that particular arrow of that particular velocity band. The hybrid BCI systems 100, 500 incorporating this navigation interface can be connected to external navigation systems like electronically operated wheelchairs. In this case, the activation of a particular arrow associated with a particular velocity band may result in the activation of movement of wheels in the wheelchair to turn or move in the desired direction. Alternatively, the hybrid BCI system 100, 500 can be presenting the user with a virtual environment that is navigable. In this case, the activation of a particular arrow in a particular velocity band in the navigation interface may allow the user to move in the virtual space presented according to the velocity and direction dictated by the activation. In other words, the UI/UX Engine 526 may modify the virtual environment presented to produce a perception of desired movement by the user. The navigation interface can also include a channel for the user to provide feedback to the navigation control system. The properties of usage of the navigation interface like duration of user selection of the symbols, resulting movement and the user's feedback can be stored as stimulus information for future use, for example for a user specific calibration and setting.

Context Based Real-World Interaction

In some embodiments, the hybrid BCI systems 100, 500 can be used to allow user interaction in an augmented or mixed reality space. That is, using the hybrid BCI system 100, 500, the real world may be relayed to the user through a pair of glasses that includes a visual field camera, as one of the peripheral sensors 108, 508, configured to capture everything that the user can see. For example, the eyeglasses and the visual field camera can be incorporated as an integral part of the video based eye-tracker 102. The eyeglasses can be configured to be integrated displays (e.g., liquid crystal displays) capable of presenting visual stimuli. Visual images or videos can be projected in the integrated displays, suitably tailored for each eye to simulate a three-dimensional space if required, allowing the user to experience augmented or mixed reality. For example, the projected images can be control interfaces like menus and buttons that can be activated or selected by implementing the pointing control and the action control features. The projected images or videos can also be rich three-dimensional environments generated to complement the real world imagery viewed by the user.

In some embodiments, the hybrid BCI systems 100, 500, can be configured to process the captured video of the real-world environment viewed by the user through the visual field camera. For example, the visual field camera (a peripheral device, 508) can record and transmit the captured real-world imagery to the I/O Unit 540 of the BCI Device 510. The Processor 520 in the BCI Device 510 can then time stamp and log the captured video via the Synchronized Event Logger 522 and Analyze the captured video in the Signal Analyzer 524. The Signal Analyzer 524 can carry out various image processing routines on the video, including image segmentation, contour detection, motion detection, image identification, etc. The Signal Analyzer 524 can use pre-obtained information stored in the memory 560 or can also obtain additional information from remote sources via communication channels established through the communicator 580, to help with the image processing routines.

Figure 8A:
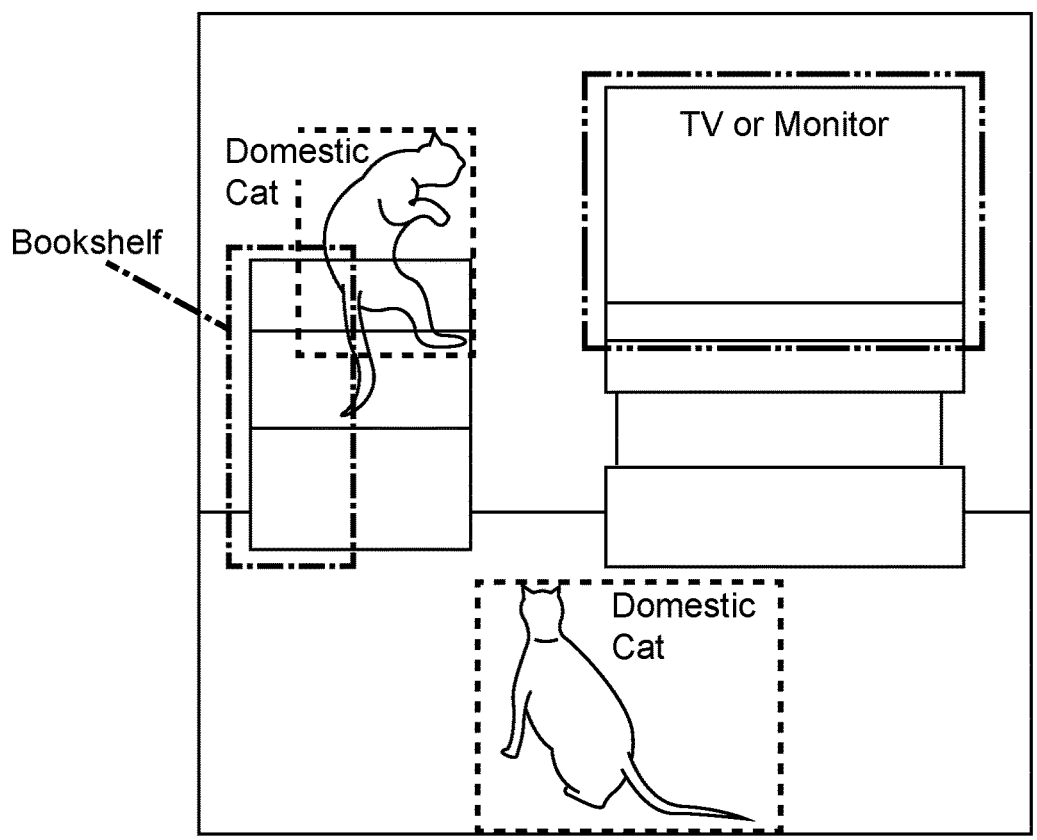
FIG. 8A shows an example of image segmentation performed on a real-world image captured by a hybrid BCI system, according to an embodiment.

FIG. 8A shows an example instance of a real world image captured by a visual field camera using one embodiment of a hybrid BCI system. The example image in FIG. 8A shows an instance of a living room of a user. For example, the Signal Analyzer 524 can receive this image in a video and segment this image into identifiable portions as highlighted in the example in FIG. 8A. That is, the Signal Analyzer 524 can detect contours and identify individual items like a television, a book shelf and two domestic cats. Further, the Signal Analyzer 524 can access stored information about the user or additional information from remote sources (e.g., websites, databases, vendor catalogs, etc.) to identify the make and model of the television in the captured video. Upon identification the Signal Analyzer 524 can determine a suitable mode of communication with the specific device identified (e.g., television of a specific make and model). Using the suitable communication channel of choice (e.g., Bluetooth, NFC, etc., which may be predetermined by the vendor) the BCI Device 510 can connect with the identified device (e.g., television) through the Communicator 580.

Figure 8B:
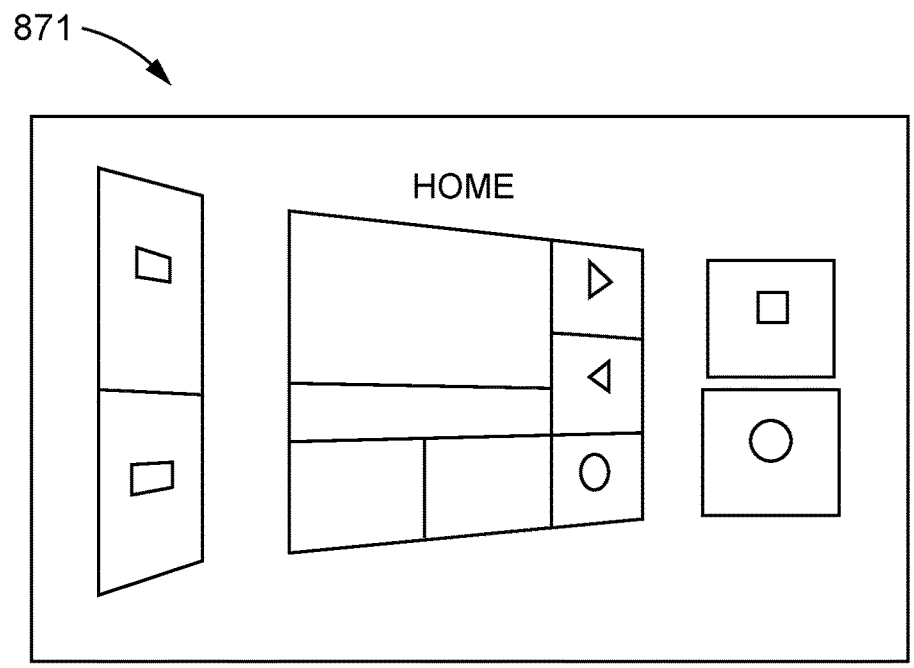
FIG. 8B shows an example UI populated with context-based control items from processing a real-world image like that shown in FIG. 8A, according to an embodiment.

In some embodiments, the identification of and successful connection to a particular controllable electronic component like a television can trigger the presentation of a context-based UI that is suitable for the identified controllable electronic device. For example, upon identification and connection to a television of a particular make and model the hybrid BCI system 100, 500 can obtain the list of controllable features of the television. The UI/UX Engine in the BCI Device 510 can then use the information about the device and the user to generate a context-based, intuitive, UI incorporating the list of available controls for the television, including items like volume control, channel control, home theater control, etc. An example UI for such a control of an example television is shown in FIG. 8B.

The context-based UI may be presented as a two or three-dimensional space and may contain symbols or icons that can be activated or inactivated through any suitable modality. The hybrid BCI system 500 can then implement the pointing control feature to detect the user's focus on a particular controllable symbol for example an 'increase volume' icon. Following which the hybrid BCI system 500 can use the neural activity recorded via a neural recording headset to implement the action control feature (e.g., activation of the increase volume icon) on the UI. This action on the context-based UI can be communicated to the television to effect change in the user's experience of the television presentation (e.g., volume) in the real-world.

Visible and Non-Visible Adaptation to UI/UX for Ease of Interaction

In some embodiments, the hybrid BCI system 100, 500 can incorporate adaptations in the generation of UI or UX to enable ease of operation with high speed and high accuracy. These adaptation may include visible properties of the UI as presented to the user. The adaptation can also include properties of the UI that not evidently visible but incorporated in the generation and maintenance of the UI or UX, and in how the pointing control and/or action control features are implemented. Some of the adaptation are disclosed below.

Focus Click-Through

In some embodiments, the hybrid BCI system 100, 500 can incorporate a three-dimensional aspect to presenting actionable menus items to the user. There may be several advantages to the presentation of actionable menus in three dimensions including the option of presenting of well-sized menu items without the appearance of clutter. Three-dimensional presentation of menu items can also be useful under conditions of limited available space for the display or presentation of visual UI or UX, as in the case of presenting augmented or mixed reality.

Figure 9A:
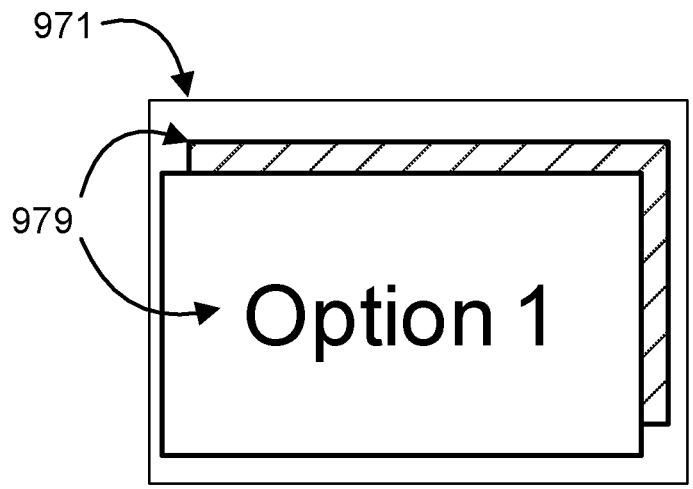
FIGS. 9A-9C show example UIs of a hybrid BCI system illustrating focus click-through adaptations, according to an embodiment.
Figure 9B:
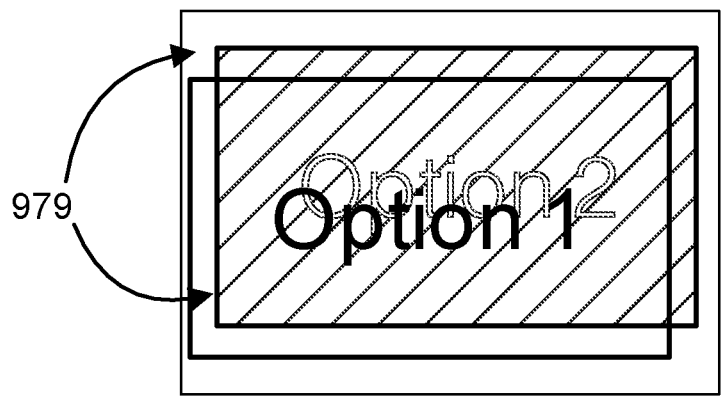
Figure 9C:
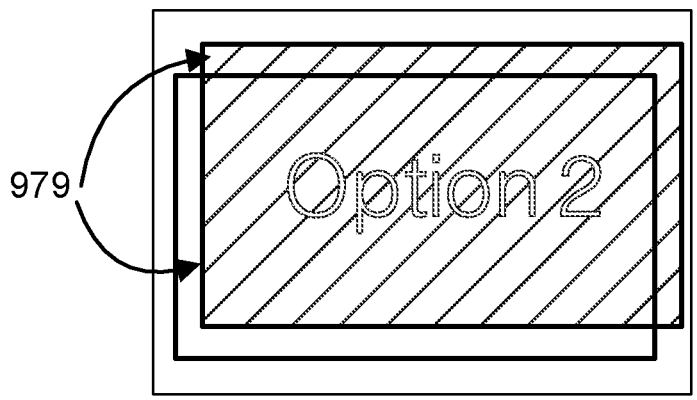

One example three-dimensional presentation in an example UI is shown in FIG. 9. The UI can include several options that can be selected to implement the action control feature by the hybrid BCI system 500. The example illustrated in FIG. 9 includes panels containing options 1 and 2. As disclosed above, the UI can be presented in three-dimensional space by taking advantage of several properties that are used to detect depth of field by the human visual system. As in the example presented in FIG. 9, the UI can modulate properties of brightness and contrast to bring specific items in or out of focus. Additionally, the UI can also use properties like occlusion of one object by another, or the perspective view of one object with respect to another to create an effect of depth in the third dimension.

During implementation of the pointing control feature the hybrid BCI system 100, 500 can sequentially present the options 1 and 2 by bringing each option in focus. The desired option can be determined by one or more method including monitoring oculomotor responses collected by the video based eye-tracker 102 to implement stereoscopic eye tracking, or correlating neural activity collected by the neural recording headset 104 with the modifications of focus depth of the options 1 and 2 in the UI, or a combination of the two. An integrated approach of using a combination of both methods can enable faster detection leading to high-speed user interactions while maintaining high accuracy of action selection.

Option Pool Pre-Selection

Figure 10A:
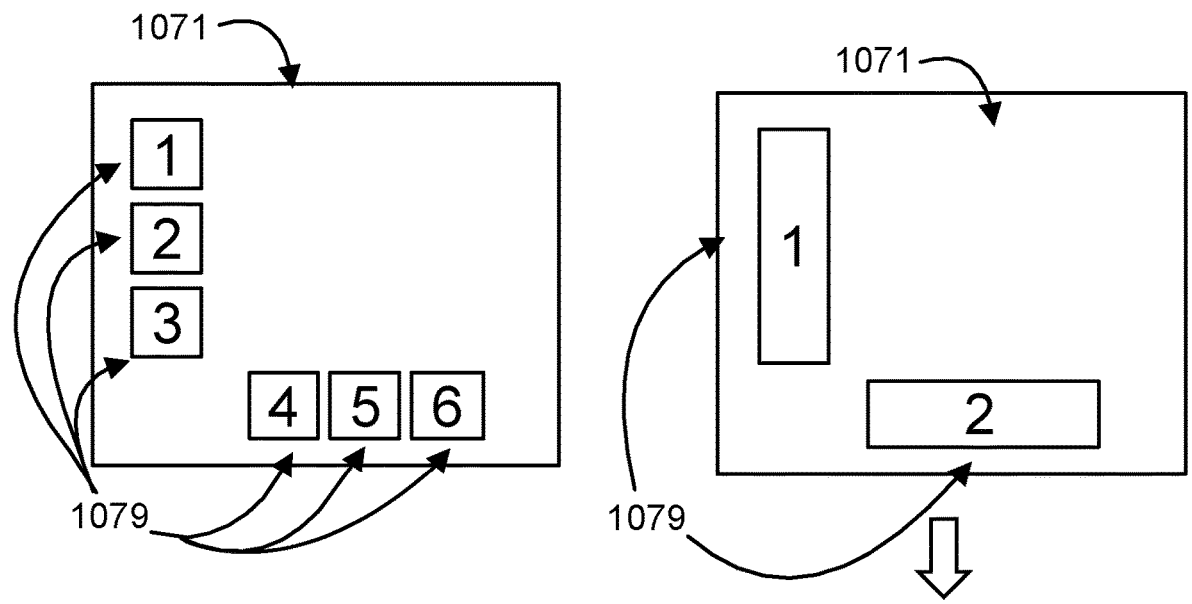
FIG. 10A illustrates an example UI of an example hybrid BCI system presenting a user with a one-step selection process, according to an embodiment.
Figure 10B:
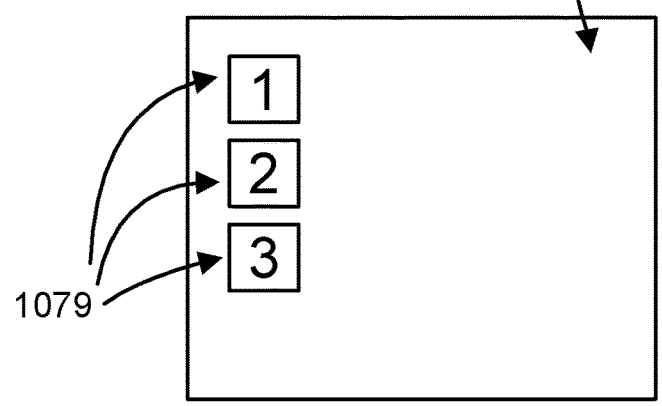
FIG. 10B illustrates another mode of a UI presenting the user with a two-step selection process implementing a pre-selection pooling adaptation, according to an embodiment.

In some embodiments, the hybrid BCI systems 100, 500 can be used to operate under conditions that have several actionable items. An example instance of a UI 1071 is shown in FIG. 10A containing six actionable items. Under certain conditions it may be suitable to reduce the number of actionable items presented at a time in the UI. This may also be to reduce uncertainty in the determination of the point of focus of the user during the implementation of the pointing control feature. It may also be to reduce uncertainty of the selected actionable item during implementation of the action control feature. Additionally, in some embodiments of the hybrid BCI systems 100, 500 the UI may be configured to flash the stimuli and correlate neural activity collected concurrently through the neural recording headset 504 to additionally use this correlational data to implement the selection of the actionable item. Under these conditions, it may be desirable to minimize repeated flashing of stimuli to enhance UX. One strategy adopted by the UI/UX Engine 524 under these requirements can be to strategically pool option items. Thus, in the example illustrated in FIGS. 10A and 10B, instead of selection one in 6 potential options in a one step process (shown in FIG. 10A) the UI can be modified to operate in a two-step process of selection. For example, in the first step, the UI may be modified to pool options 1, 2, and 3 together to form a pooled, pre-selection option 1, and pool options 4, 5, and 6 together to form a pooled, pre-selection option 2. Thus the user may point to and select one of two possible pre-selection options in the first step. Upon implementing the pointing control and selection control features on the pre-selection options in this first step the UI can then change to present the actual individual options contained in the pre-selection option 1 or the pre-selection option 2, depending on whichever may be selected in the first step, as shown in FIG. 10B. While this procedure may increase the number of steps involved in selection, the process of pooling options into pre-selection pools may reduce the number of flashes of the individual options. Additionally, the accuracy of selecting the correct option may increase due to reduced uncertainty in both the first and second steps.

Draggable Marker

The hybrid BCI system 100 or 500 can operate by using a visual aid (e.g., a cursor) to indicate the current status of the pointing control feature. The cursor may be a symbol or a marker whose properties (e.g., color, shape brightness, etc.) can be used to indicate the current status of the system while implementing the pointing control and the action control features. For example, the marker can be plain while pointing but be modified into a different color signifying completion of implementation of the pointing control (i.e., selection of an option presented in the UI). The marker can further be modified into a yet another shape or color to signify the completion of implementing the action control feature (i.e., activation of an option).

In some embodiments of the hybrid BCI system 100, 500, the marker or cursor can be simply moved by following the trajectory of eye movements registered by eye-tracking. Thus, possible items that can be selected in the UI are items whose position on the UI intersect with the trajectory of the marker (following the trajectory of the user's eyes). Selection may be implemented by several methods including mere focusing, or a timed foveation on an object, etc.

Figure 11A:
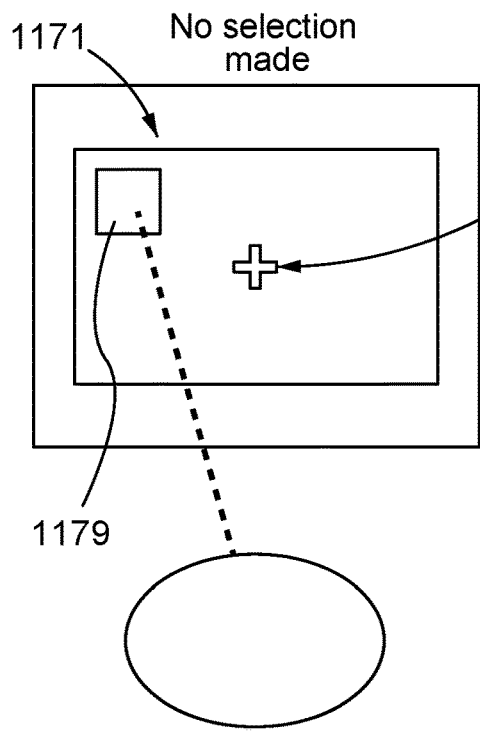
FIGS. 11A-11D show an example UI of a hybrid BCI system, illustrating the implementation of a draggable marker adaptation, according to an embodiment.
Figure 11B:
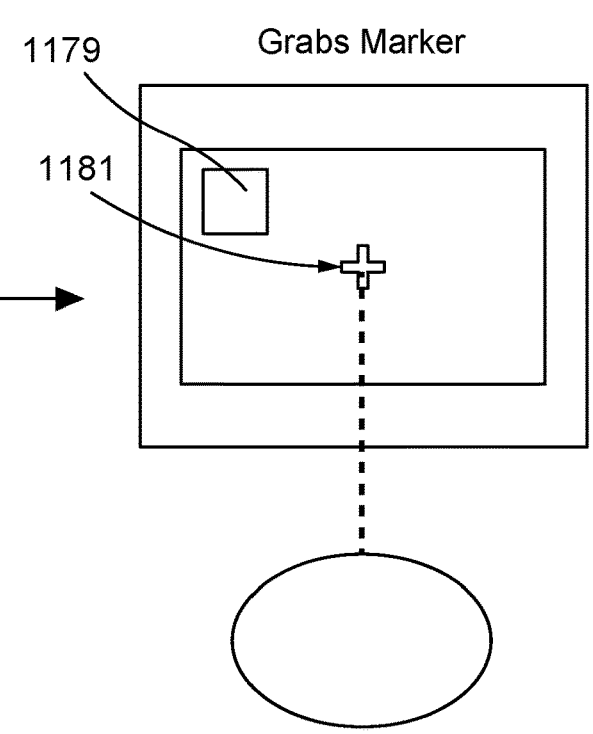
Figure 11C:
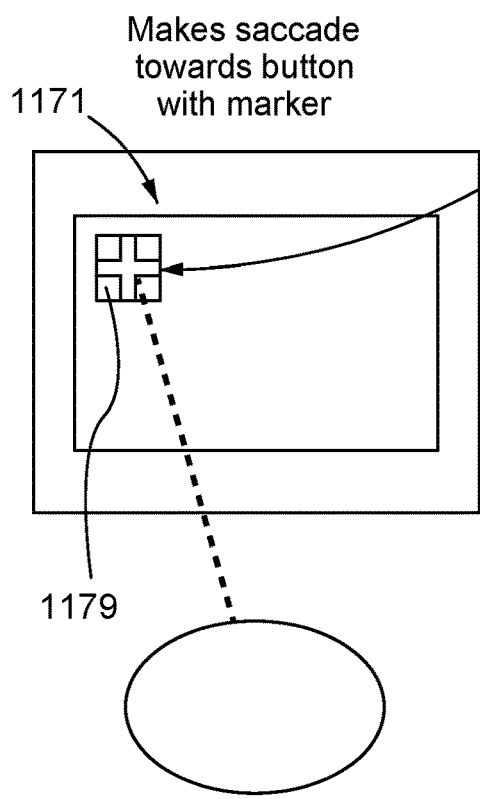
Figure 11D:
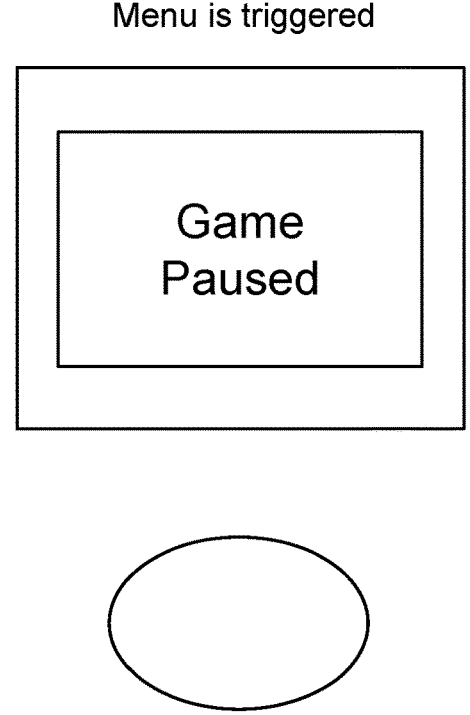

In some embodiments, the marker can be modified to not closely follow the trajectory of the user's eye but instead be a draggable, sticky marker. That is, in some embodiments of the hybrid BCI system 100, 500, the UI may be switched to an operating mode that includes a sticky marker that can be dragged and dropped from one object or option to another. FIGS. 11A and 11B illustrate an example UI 1171 including a sticky marker 1181. In the example shown, the user interacts with the UI 1171 by dragging the sticky marker 1181 from a home position at the center of the display and placing the sticky marker 1181 onto the option to be selected 1179. For example, the UX presented in FIG. 11 may be a video game. The user may want to pause the game while the game is in progress. This can be achieved by using the sticky marker 1181. The user can 'pick up' the sticky marker 1181 from its home position at the center of the display by foveating over to its home position. Then, by 'dragging' the sticky marker 1181, the user can foveate to the option to be selected, for example the 'pause' option indicated by the block icon 1179. By foveating to the option 1179 while dragging the sticky marker the user can then 'drop' the sticky marker 1181 over the pause option 1179 as shown in FIG. 11B. The sticky marker 1181 then sticks to the selected option 1179, completing the implementation of the pointing control feature.

In embodiments of the hybrid BCI system operating in modes that use the sticky marker 1181, any mere foveation or saccadic eye movement of the user without having 'picked up' the sticky marker 1181 will not have any effect of selecting or implementing the pointing control feature. This can lead to reduction of spurious selections by stray gazes or stray fixations by the user's eyes. Additionally, the user will not be required to make foveations or eye movements timed to be long enough to implement the pointing control feature which may be required without the use of a sticky marker. Thus, the use of sticky markers can improve the ease of user interaction with high-speed and accurate pointing and selection while not requiring unnatural and/or disruptively long fixations by the user.

Another example of implementing a sticky marker, using an embodiment of the hybrid BCI systems 100,500, is shown in FIGS. 12A-12H. Specifically, FIGS. 12A-12H show the sequence of events when using a sticky marker to select options. For example, in FIG. 12A the example UI 1271 shows four potential options A, B, C and D 1279 and a sticky marker 1281 placed in its home position at the center of the screen. The UI 1271 also includes a sticky grabber object 1285 that indicates the status the pointing control feature and aids in the process of dragging the sticky marker 1281 as described below. The UI also includes a special option 1283 indicated by a symbol of a recycle bin. The interface 1271 is repeatedly presented in FIGS. 12B-12H indicating the sequence of changes resulting from user interaction during the usage of the sticky marker 1281.

For example, in FIG. 12A the sticky marker 1281 is in the home position and the sticky grabber 1285 is colored a first color (e.g., blue) and is empty. If the user desired to select the option B, for example, the user begins by pointing his/her gaze at the sticky marker 1281 in the home position. This results in the sticky marker 1281 being grabbed by the sticky grabber 1285 as shown in FIG. 12B. Notably, there is not minimum fixation duration required for the user to 'pick up' the sticky marker 1281. Just the mere passing of the user's gaze over the home position of the sticky marker 1281 can result in it being grabbed by the sticky grabber 1285.

Following grabbing the sticky marker 1281 onto the sticky grabber 1285 the user can pass their gaze onto the option they want to select, for example option B. The mere crossing of the user's gaze onto an option can result in the marker being dragged onto that option, as shown in FIG. 12C. The option does not get selected immediately. A timer 1287 that may or may not be visible to the user can start as soon as the sticky marker 1281 is dragged onto an option. The selection of the option can be realized once the timer 1287 times out after a preset amount of time.

However, if the user chooses to select another option, for example option D, before the timer 1287 times out, this can be done by the user passing their gaze on the option B with the sticky marker 1281. This picks up the sticky marker 1281 back onto the sticky grabber 1285 as indicated by FIG. 12E. Following this the user can then pass their gaze onto the option to be selected, for example option D, which results in the sticky marker 1281 being dragged onto the option D, as shown in FIG. 12F.

If the user inadvertently picks up the sticky marker 1281 during some other action, they can trash the sticky marker 1281 by glancing at the recycle bin icon 1283, as indicated bin FIG. 12F. Similarly, if the user inadvertently drops the sticky marker 1281 onto an undesired option they can null this selection by passing their back on the undesired option with the sticky marker 1281 and then gaze at the recycle bin icon 1283.

Selection Activation

In some embodiments of the hybrid BCI systems 100, 500, the UI can be adapted to provide a convenient mechanism for activating and/or deactivating specific important symbols that may be central to operating the hybrid BCI system in that context. For example, when a hybrid BCI system is used to run UI/UX interfaces controlling certain specific applications or associated devices the UI may contain an associated main symbol or icon that upon selection can centrally control several aspects of that specific application or connected device.

One example application can be a video based game that can be presented through a UI that is centrally controlled by a Core Icon. The Core Icon upon selection can bring up several menus that control the game play, control inventory of the user during gameplay etc. Thus the user can access these menus by selecting the Core Icon when required. Thus, the constant presence of the Core Icon is desired during the use of the hybrid BCI system for game play. However, the Core Icon may not be constantly needed during the game play.

In some embodiments, the constant requirement of a control icon, such as a Core Icon, can be handled by placing the Core Icon somewhere on the displayed UI in a location that is non-obstructive to the primary environment, for example the game environment in this case. As shown in an example UI 1371 in FIG. 13A, the non-obstructively placed control icon 1379 can be an example Core Icon that is a small, semi-transparent "n". FIG. 13A illustrates how the example Core Icon 1379 may appear on a screen with the UI 1371, under normal circumstances of ongoing usage of the UI 1371.

FIGS. 13B-13D show an example instantiation of the above mentioned Selection Activation process through the Core Icon 1379 in the UI 1371. For example, during an ongoing interaction with the UI 1371 the user may want to access the controls available through the Core Icon 1379. The user may foveate towards the Core Icon 1379. Once the oculomotor eye tracking signals are analyzed to indicate that the user's gaze is fixated on or proximate to the Core Icon 1379 (indicated in FIG. 13B), the UI 1371 can be modified to change the appearance of the icon 1379. For example, the UI 1371 can change the appearance of the Core Icon 1379 from being semi-transparent into being solid and/or opaque. The solidified Core Icon 1379, indicated by the solid, colored 'n' in FIG. 13C, can then be made to change the appearance again. For example, this change in appearance (e.g. pulsing of the Core Icon 1379) can be used to indicate that the Core Icon 1379 can now be selected if desired. If the user's gaze moves away from the Core Icon 1379 during the time period that the Core Icon 1379 changes in appearance, the change in appearance can stop and the Core Icon 1379 can return to the unchanged state, for example as indicated in FIG. 13A. In the operation of the Core Icon 1379, the UI 1371 may or may not use Ghost Flashes, described below.

The UI 1371 can employ invisible flashes or ghost flashes that can be used as a fundamental UI tool by the processor 520 of a hybrid BCI system to detect relevant oculomotor response or relevant neural activity associated with any stimulus presented. There can be several different uses to employing ghost flashes in a controlled manner in a UI. For example, ghost flashes can be employed to gauge user response to a flash of any visible stimulus. That is, any concurrent oculomotor or neural response during a ghost flash can be used as a true negative response. Such a true negative response can be used to set one or more thresholds that have to be crossed for detection of a relevant, stimulus triggered, oculomotor or neural response. Ghost flashes can be used in the implementation of the selection activation adaptation of the UI to distinguish a true selection from a spurious selection due to a stray gaze.

Icons or symbols displayed on the UI can be made available to be manipulated by a user. And the availability of the icon or symbol can be indicated to the user via a temporary or transient change in their appearance. The change in appearance can be suitably long and/or salient such that the user may be alerted to register the change. Changes in appearance can be implemented through altering any of several properties of an icon. For example, through flashing by altering the brightness intensity, contrast, color, size, shape, position etc. The change in appearance is described as a flash herein, as an example.

In some embodiments, for example, each change of the Core Icon can be counted as a "Tag change" (e.g. a tag flash) which can be a single change in appearance of an option icon, for example 1379. A tag change can be a change in appearance (e.g. flashing, pulsing etc.) tied to an icon or object displayed on the UI (e.g. UI 1371). Several option icons can flash together in groups called a flash group or a single option icon, like the Core Icon, can form a flash group by itself. Ghost Flashes can occur between the slow pulses and/or flashes of the Neurable icon in a portion of the UI adjacent to the Core Icon. Ghost flashes can be configured to occur either singly or in groups forming a flash group. The Ghost Flashes can be used to set a selection threshold. When a oculomotor response and/or a neural activity response crosses the threshold set by the ghost flashes, the UI 1371 can bring up a selection menu populated by several selectable options, for example options 1379 indicated by A, B, C and D in FIG. 13D. Following the presentation of the selection menu the user can select and trigger the action associated with each selectable option by implementing the pointing control feature and the action control feature described above. If eye tracking analysis determines that user gaze position is no longer fixated around the selection menu area, the menu can be deactivated and the transparent Core Icon can reappear.

CONCLUSION

In summary, systems and methods are described herein for use in the implementation of an integrated hybrid Brain Computer Interface operable by a user in real-time. The disclosed system includes an eye-movement tracking system to implement a pointing control feature and a brain activity tracking system to implement an action control feature. Both features are implemented through the presentation of a UI strategically designed to enable high speed and accurate operation. Additionally, the disclosed systems and methods are configured to be hardware agnostic to implement a real-time hybrid BCI on any suitable platform to mediate user manipulation of virtual, augmented or real environments.

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above Where schematics and/or embodiments described above indicate certain components arranged in certain orientations or positions, the arrangement of components may be modified. While the embodiments have been particularly shown and described, it will be understood that various changes in form and details may be made. Any portion of the apparatus and/or methods described herein may be combined in any combination, except mutually exclusive combinations. The embodiments described herein can include various combinations and/or sub-combinations of the functions, components, and/or features of the different embodiments described.

The invention claimed is:
1. An apparatus, comprising:
a display configured to present a control interface to a user;
an eye-tracking device configured to record eye-movement signals associated with the user;
a neural recording device configured to record neural signals associated with the user;
an interfacing device operatively coupled to the display, the eye-tracking device, and the neural recording device, the interfacing device including:
a memory; and
a processor operatively coupled to the memory and configured to:
receive the eye-movement signals from the eye-tracking device and the neural signals from the neural recording device;
generate and present a stimulus, via the control interface and to the user, the stimulus including a set of control items, each control item from the set of control items associated with an action from a set of actions;
provide a sticky control item configured to be (1) transitioned to a picked-up state in response to an eye-movement signal indicating a foveation over the sticky control item, (2) moved based on an eye-movement signal of the user, and (3) transitioned to a dropped state on a target control item to activate the target control item;
provide a grabber object configured to manipulate the sticky control item;
associate the sticky control item with the grabber object when the sticky control item is transitioned to the picked-up state based on an eye-movement signal indicating a foveation on the sticky control item;
determine a point of focus of the user based on at least one of the eye-movement signals or the neural signals, the point of focus being associated with an identified control item from the set of control items;
dissociate, when the sticky control item is at the dropped state and on the identified control item, the sticky control item from the grabber object and associate the sticky control item with the identified control item;
and
activate the identified control item to implement an action intended by the user.
2. The apparatus of claim 1, wherein:
the eye-tracking device includes an optical sensor,
the neural signals include electroencephalogram (EEG) signals including at least one of a visually evoked potential, a sensory evoked potential, a motor imagery signal, an Event Related Potential (ERP), a sensorimotor rhythm, an event related desynchronization (ERD), an event related synchronization (ERS), a slow cortical potential (SCP), and a brain state dependent signal, and
the processor is further configured to integrate the eye-movement signals and the EEG signals to determine the point of focus of the user.
3. The apparatus of claim 1, wherein the display is configured to present the control interface as a three-dimensional space.
4. The apparatus of claim 1, wherein the stimulus includes at least one of a visual stimulus, an auditory stimulus, vestibular stimulus, and a haptic stimulus.
5. The apparatus of claim 1, wherein the set of control items associated with controlling navigation through a virtual environment.
6. The apparatus of claim 5, wherein the set of control items include: a first subset of control items associated with controlling a velocity of virtual movement of the user, and a second subset of control items associated with controlling a direction of virtual movement of the user.
7. The apparatus of claim 1, wherein the display is further configured to present a view of a real-world environment and is configured to present the control interface over the view of the real-world environment.
8. The apparatus of claim 1, wherein:
the set of control items is a first set of control items, the stimulus is a first stimulus,
the display is further configured to present a view of a real-world environment and is configured to present the control interface over the view of the real-world environment, and
the processor is further configured to:
receive a set of images associated with the real-world environment;

analyze the set of images to identify at least one machine operatively connected to the processor;

obtain information of a set of actions associated with the machine;

generate a second set of control items based on the information; and present, via the control interface and to the user, a second stimulus including the second set of control items.

9. The apparatus of claim 1, wherein the stimulus includes a core icon, placed at a predetermined location on the control interface, the core icon configured to be activated based on the point of focus of the user being on the core icon and lasting a duration greater than a threshold value, the threshold value determined based on a response from the user associated with a presentation of a flash stimulus.

10. The apparatus of claim 9, wherein the flash stimulus is invisible.

11. A non-transitory processor-readable medium storing code representing instructions to be executed by a processor, the instructions comprising code to cause the processor to:

generate a control interface configured to be manipulated, by a user, to perform a set of actions;

generate and present a stimulus, via the control interface and to the user, the stimulus including a set of control items, each control item from the set of control items being associated with an action from a set of actions, the set of control items;

receive information from an eye-tracking device including eye-movement signals associated with the user, the eye-tracking device;

determine, based on the information from the eye-tracking device, a point of focus of the user;

identify a first control item, from the set of control items, associated with the point of focus of the user at a first time;

provide a grabber object included in the control interface, the grabber object being configured to manipulate a sticky control item included in the set of control items;

identify the first control item as a sticky control item configured to be (1) transitioned to a picked-up state in response to an eye-movement signal indicating a foveation on the sticky control item, (2) moved based on the user's eye-movement signal, and (3) transitioned to a dropped state on a target control item to activate the target control item;

associate, when the sticky control item is at the picked-up state and based on the sticky control item being associated with the point of focus of the user at the first time, the sticky control item with the grabber object;

determine a point of focus of the user at a second time after the first time, identify a second control item associated with the point of focus of the user at the second time, the second control item being different from the sticky control item;

dissociate, when the sticky control item is at the dropped state and on the second control item, the sticky control item from the grabber object and associate the sticky control item with the second control item; and determine, based on the association between the sticky control item and the second control item, an action intended by the user.

12. The non-transitory processor-readable medium of claim 11, wherein the instructions further comprising code to cause the processor to execute the action intended by the user.

13. The non-transitory processor-readable medium of claim 11, wherein the instructions further comprising code to cause the processor to:

present to the user an indication of the action intended by the user for confirmation by the user; and in response to receiving a signal representing a confirmation by the user, execute the action intended by the user.

14. The non-transitory processor-readable medium of claim 11, wherein the instructions further comprise code to cause the processor to receive information from a neural recording device associated with the user, the neural information including electroencephalogram (EEG) signals, the EEG signals including at least one of a visually evoked potential, a sensory evoked potential, a motor imagery signal, an Event Related Potential (ERP), a sensorimotor rhythm, an event related desynchronization (ERD), an event related synchronization (ERS), a slow cortical potential (SCP), and a brain state dependent signal, and the code to cause the processor to determine the point of focus includes code to cause the processor to integrate the eye-movement signals and the EEG signals to determine the point of focus of the user.

15. The non-transitory processor-readable medium of claim 11, wherein the code to cause the processor to present the stimulus includes code to cause the processor to present the set of control items in a three-dimensional virtual space defined by the control interface.

16. The non-transitory processor-readable medium of claim 11, wherein the instructions further comprise code to cause the processor to group the set of control items into a set of groups, the code to cause the processor to present the stimulus includes code to cause the processor to present the set of the control items as grouped in the set of groups.

17. The non-transitory processor-readable medium of claim 11, wherein the set of control items includes a draggable control item, the draggable control item configured to be manipulated based on eye-movement signals associated with the user.

18. The non-transitory processor-readable medium of claim 17, the instructions further comprising code to cause the processor to:

identify the first control item as a draggable control item, the draggable control item configured to be manipulated based on eye-movement signals associated with the user and included in the information received from the eye-tracking device;

determine a point of focus of the user at a second time after the first time;

move the draggable control item to a location associated with the point of focus of the user at the second time;

identify a second control item associated with the point of focus of the user at the second time, the second control item being different from the draggable control item;

determine, based on the second control item, the action intended by the user.

19. The non-transitory processor-readable medium of claim 11, wherein the stimulus includes a core icon, placed at a predetermined location on the control interface, the core icon configured to be activated based on a point of focus of the user being on the core icon and lasting a duration greater than a threshold value, the threshold value determined based on a response from the user associated with a presentation of a flash stimulus.

20. The non-transitory processor-readable medium of claim 19, the instructions further comprising code to cause the processor to:

receive information from a neural recording device, the eye-tracking device and the neural recording device configured to monitor behavior of the user; and determine the point of focus of the user based on the information from the eye-tracking device or the information from the neural recording device.

21. A method, comprising:

presenting, to a user, at a first time period, a stimulus via an control interface, the stimulus including control items associated with a set of actions, the control items including a sticky control item configured to be (1) transitioned to a picked-up state in response to a foveation of the user on the sticky control item, (2) moved based on an eye-movement signal of the user, and (3) transitioned to a dropped state on a target control item to activate the target control item;

receiving, from an eye-tracking device, a first set of inputs including eye-movement signals of the user at the first time period;

identifying, based on the eye-movement signals, a foveation over a sticky control item;

transitioning the sticky control item to the picked-up state in response to the foveation over a sticky control item;

associating the sticky control item with a grabber object configured to manipulate the sticky control item;

determining a point of focus of the user at a second time after the first time, identifying a second control item associated with the point of focus of the user at the second time, the second control item being different from the sticky control item;

transitioning the sticky control item to the dropped state;

dissociating, when the sticky control item is at the dropped state and on the second control item, the sticky control item from the grabber object and associating the sticky control item with the second control item; and determining, based on the association between the sticky control item and the second control item, an action intended by the user.

22. The method of claim 21, wherein the second control item is a dynamic visual stimulus, the method further comprising:

detecting a movement of the dynamic visual stimulus;

tracking the movement of the dynamic visual stimulus;

tagging the dynamic visual stimulus;

identifying an event associated with the dynamic visual stimulus; and modifying the control interface based on the event associated with the dynamic visual stimulus.

23. The method of claim 21, further comprising:

receiving neural signals from a neural recording device, the neural signals including electroencephalogram (EEG) signals, the EEG signals including at least one of a visually evoked potential, a sensory evoked potential, a motor imagery signal, an Event Related Potential (ERP), a sensorimotor rhythm, an event related desynchronization (ERD), an event related synchronization (ERS), a slow cortical potential (SCP), and a brain state dependent signal; and integrating the eye-movement signals and the EEG signals to determine a point of focus of the user.

* * * * *

UNITED STATES PATENT AND TRADEMARK OFFICE
CERTIFICATE OF CORRECTION

| | |
|---|---|
| PATENT NO. | : 12,001,602 B2 |
| APPLICATION NO. | : 16/872730 |
| DATED | : June 4, 2024 |
| INVENTOR(S) | : Ramses Alcaide et al. |

It is certified that error appears in the above-identified patent and that said Letters Patent is hereby corrected as shown below:

In the Specification

At Column 11, Line number 35, reads:
"UL/UX"
Should read:
--UI/UX--

In the Claims

At Column 29, Claim number 11, Line number 31-32, reads:
"eye-movement signals associated with the user, the eye-tracking device"
Should read:
--eye-movement signals associated with the user--

Signed and Sealed this
Twenty-eighth Day of October, 2025

John A. Squires
*Director of the United States Patent and Trademark Office*